United States Patent
Gao et al.

(10) Patent No.: US 10,247,662 B2
(45) Date of Patent: Apr. 2, 2019

(54) INTEGRATED COMPUTATIONAL ELEMENTS WITH FREQUENCY SELECTIVE SURFACE

(71) Applicant: Halliburton Energy Services, Inc., Houston, TX (US)

(72) Inventors: Li Gao, Katy, TX (US); Michael T. Pelletier, Houston, TX (US); David L. Perkins, Conroe, TX (US); Neal Gregory Skinner, Lewisville, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 271 days.

(21) Appl. No.: 14/900,017

(22) PCT Filed: Jul. 9, 2013

(86) PCT No.: PCT/US2013/049693
§ 371 (c)(1),
(2) Date: Dec. 18, 2015

(87) PCT Pub. No.: WO2015/005904
PCT Pub. Date: Jan. 15, 2015

(65) Prior Publication Data
US 2016/0146724 A1    May 26, 2016

(51) Int. Cl.
*G01J 3/02* (2006.01)
*G01N 21/25* (2006.01)
(Continued)

(52) U.S. Cl.
CPC .......... *G01N 21/255* (2013.01); *E21B 49/08* (2013.01); *G01J 3/0205* (2013.01); *G01J 3/28* (2013.01);
(Continued)

(58) Field of Classification Search
CPC ...... G01N 21/255; G01N 21/27; G01N 33/24; G01N 2201/068; G01J 3/0205; G01J 3/28; G01J 3/457; G02B 5/204; E21B 49/08
See application file for complete search history.

(56) References Cited

U.S. PATENT DOCUMENTS

| 5,075,550 A | 12/1991 | Miller et al. |
| 5,399,229 A | 3/1995 | Stefani et al. |

(Continued)

FOREIGN PATENT DOCUMENTS

| EP | 1969326 | 9/2008 |
| EP | 2087328 | 8/2009 |

(Continued)

OTHER PUBLICATIONS

Authorized officer Ahn, Jae Yul, International Search Report and Written Opinion for PCT/US2013/049697, dated Apr. 11, 2014, 11 pages.

(Continued)

*Primary Examiner* — Christine S. Kim
(74) *Attorney, Agent, or Firm* — Benjamin Fite; Parker Justiss, P.C.

(57) ABSTRACT

Technologies are described for providing optical analysis systems using an integrated computational element that has a surface patterned to selectively reflect or transmit different wavelengths by differing amounts across a spectrum of wavelengths. In one aspect, a measurement tool contains an optical element including a layer of material patterned so that the optical element selectively transmits or reflects, during operation of the measurement tool, light in at least a portion of a wavelength range by differing amounts, the differing amounts being related to a property of a sample. The wavelength range can include wavelengths in a range from about 0.2 μm to about 100 μm. Additionally, the sample (Continued)

can include wellbore fluids and the property of the sample is a property of the wellbore fluids.

25 Claims, 9 Drawing Sheets

(51) Int. Cl.

| | | |
|---|---|---|
| *E21B 49/08* | (2006.01) | |
| *G01N 21/27* | (2006.01) | |
| *G01N 33/24* | (2006.01) | |
| *G01J 3/28* | (2006.01) | |
| *G01J 3/457* | (2006.01) | |
| *G02B 5/20* | (2006.01) | |

(52) U.S. Cl.
CPC .............. *G01J 3/457* (2013.01); *G01N 21/27* (2013.01); *G01N 33/24* (2013.01); *G02B 5/20* (2013.01); *G02B 5/201* (2013.01); *G02B 5/204* (2013.01); *G01N 2201/068* (2013.01)

(56) References Cited

U.S. PATENT DOCUMENTS

| | | | |
|---|---|---|---|
| 5,453,716 | A | 9/1995 | Person et al. |
| 5,537,479 | A | 7/1996 | Kreisel et al. |
| 5,619,366 | A | 4/1997 | Rhoads et al. |
| 6,078,389 | A | 6/2000 | Zetter |
| 6,154,550 | A | 11/2000 | Beyer |
| 6,163,259 | A | 12/2000 | Barsumian et al. |
| 6,198,531 | B1 | 3/2001 | Myrick et al. |
| 6,213,250 | B1 | 4/2001 | Wisniewski et al. |
| 6,218,978 | B1 | 4/2001 | Simpkin et al. |
| 6,232,931 | B1* | 5/2001 | Hart .................... H01Q 15/002 343/776 |
| 6,529,276 | B1 | 3/2003 | Myrick |
| 6,646,753 | B2 | 11/2003 | Zhang et al. |
| 6,774,517 | B2 | 6/2004 | Forno et al. |
| 6,804,060 | B1 | 10/2004 | Tsai et al. |
| 6,905,578 | B1 | 6/2005 | Moslehi et al. |
| 6,965,431 | B2 | 11/2005 | Vo-Dinh et al. |
| 7,123,844 | B2 | 10/2006 | Myrick |
| 7,138,156 | B1 | 11/2006 | Myrick et al. |
| 7,163,901 | B2 | 1/2007 | Downey |
| 7,166,797 | B1* | 1/2007 | Dziendziel ............. G02B 5/204 136/246 |
| 7,332,044 | B2 | 2/2008 | Sidorin et al. |
| 7,332,094 | B2 | 2/2008 | Abney et al. |
| 7,472,748 | B2 | 1/2009 | Gdanski et al. |
| 7,623,233 | B2 | 11/2009 | Freese et al. |
| 7,679,563 | B2 | 3/2010 | Werner et al. |
| 7,697,141 | B2 | 4/2010 | Jones et al. |
| 7,712,527 | B2 | 5/2010 | Roddy |
| 7,753,847 | B2 | 7/2010 | Greenleaf et al. |
| 7,777,870 | B2 | 8/2010 | Hayes et al. |
| 7,792,644 | B2 | 9/2010 | Kotter et al. |
| 7,828,929 | B2 | 11/2010 | Lee et al. |
| 7,834,999 | B2 | 11/2010 | Myrick et al. |
| 7,911,605 | B2 | 3/2011 | Myrick et al. |
| 7,920,258 | B2 | 4/2011 | Myrick et al. |
| 7,934,556 | B2 | 5/2011 | Clark et al. |
| 8,054,212 | B1 | 11/2011 | Holly et al. |
| 8,106,850 | B1 | 1/2012 | Gregoire et al. |
| 8,141,633 | B2 | 3/2012 | Hampton et al. |
| 8,164,061 | B2 | 4/2012 | Pawlak et al. |
| 8,216,161 | B2 | 7/2012 | Darlington et al. |
| 8,252,112 | B2 | 8/2012 | Ovshinsky |
| 2004/0233508 | A1 | 11/2004 | Kosc |
| 2005/0054928 | A1 | 3/2005 | Cerofolini |
| 2007/0282647 | A1 | 12/2007 | Freese et al. |
| 2008/0231849 | A1 | 9/2008 | Myrick et al. |
| 2008/0238801 | A1 | 10/2008 | Ragan |
| 2008/0276687 | A1 | 11/2008 | Myrick et al. |
| 2009/0073433 | A1 | 3/2009 | Myrick et al. |
| 2009/0097024 | A1 | 4/2009 | Blackburn et al. |
| 2009/0140144 | A1 | 6/2009 | Myrick et al. |
| 2009/0154288 | A1 | 6/2009 | Heathman |
| 2009/0182693 | A1 | 7/2009 | Fulton et al. |
| 2009/0216504 | A1 | 8/2009 | Priore et al. |
| 2009/0219512 | A1 | 9/2009 | Myrick et al. |
| 2009/0219538 | A1 | 9/2009 | Myrick et al. |
| 2009/0219539 | A1 | 9/2009 | Myrick et al. |
| 2009/0250613 | A1 | 10/2009 | Myrick et al. |
| 2009/0299946 | A1 | 12/2009 | Myrick et al. |
| 2009/0316150 | A1 | 12/2009 | Myrick et al. |
| 2010/0050905 | A1 | 3/2010 | Lewis et al. |
| 2010/0051266 | A1 | 3/2010 | Roddy et al. |
| 2010/0051275 | A1 | 3/2010 | Lewis et al. |
| 2010/0073666 | A1 | 3/2010 | Perkins et al. |
| 2010/0141952 | A1 | 6/2010 | Myrick et al. |
| 2010/0149537 | A1 | 6/2010 | Myrick et al. |
| 2010/0153048 | A1 | 7/2010 | Myrick et al. |
| 2010/0182600 | A1 | 7/2010 | Freese et al. |
| 2010/0195076 | A1 | 8/2010 | Myrick et al. |
| 2010/0238801 | A1 | 9/2010 | Smith et al. |
| 2010/0245096 | A1 | 9/2010 | Jones et al. |
| 2010/0265509 | A1 | 10/2010 | Jones et al. |
| 2010/0271285 | A1 | 10/2010 | Yun et al. |
| 2010/0302539 | A1 | 12/2010 | Myrick et al. |
| 2010/0305741 | A1 | 12/2010 | Myrick |
| 2010/0328669 | A1 | 12/2010 | Myrick et al. |
| 2011/0048708 | A1 | 3/2011 | Glasbergen et al. |
| 2011/0093205 | A1 | 4/2011 | Bern |
| 2011/0163046 | A1 | 7/2011 | Neal et al. |
| 2011/0199610 | A1 | 8/2011 | Myrick et al. |
| 2012/0268744 | A1 | 10/2012 | Wolf et al. |
| 2013/0284894 | A1 | 10/2013 | Freese et al. |
| 2013/0284895 | A1 | 10/2013 | Freese et al. |
| 2013/0284896 | A1 | 10/2013 | Freese et al. |
| 2013/0284897 | A1 | 10/2013 | Freese et al. |
| 2013/0284898 | A1 | 10/2013 | Freese et al. |
| 2013/0284899 | A1 | 10/2013 | Freese et al. |
| 2013/0284900 | A1 | 10/2013 | Freese et al. |
| 2013/0284901 | A1 | 10/2013 | Freese et al. |
| 2013/0284904 | A1 | 10/2013 | Freese et al. |
| 2013/0286398 | A1 | 10/2013 | Freese et al. |
| 2013/0286399 | A1 | 10/2013 | Freese et al. |
| 2013/0287061 | A1 | 10/2013 | Freese et al. |
| 2014/0131559 | A1* | 5/2014 | Yen .................... G02B 1/002 250/221 |
| 2014/0209788 | A1* | 7/2014 | Moddel ................ G01J 3/0205 250/208.2 |
| 2014/0298900 | A1* | 10/2014 | Clarke .................... E21B 49/00 73/152.55 |

FOREIGN PATENT DOCUMENTS

| | | | |
|---|---|---|---|
| EP | 2140238 | 1/2010 | |
| KR | 10-2011-0075539 | 7/2011 | |
| KR | 2013/0017718 | 2/2013 | |
| WO | WO 9400891 A1 * | 1/1994 | ............ G02B 5/204 |
| WO | WO 2004/015364 | 2/2004 | |
| WO | WO 2005/093904 | 10/2005 | |
| WO | WO 2006/031733 | 3/2006 | |
| WO | WO 2006/137902 | 12/2006 | |
| WO | WO 2007/064575 | 6/2007 | |
| WO | WO 2007/015115 | 8/2007 | |
| WO | WO2011/103066 | 8/2011 | |
| WO | WO2013/022556 | 2/2013 | |
| WO | WO2014/042642 | 3/2014 | |

OTHER PUBLICATIONS

Authorized officer Cha, Young Lan, International Search Report and Written Opinion for PCT/US2013/049693, dated Mar. 20, 2014, 12 pages.

Commissioner, International Search Report and Written Opinion for PCT/US2014/042368, dated Mar. 13, 2015, 15 pages.

Gdanski et al., "Using Lines-of-Solutions to Understand Fracture Conductivity and Fracture Cleanup," SPE 142096, SPE Production

(56) References Cited

OTHER PUBLICATIONS and Operations Symposium held in Oklahoma City, OK, Mar. 27-29, 2011, 16 pages.
Telemark, "Model 820 In-Situ Spectroscopic Optical Monitor," Dec. 2010, 4 pages.
J.A. Woollam Co., Inc., Characterizing Processes with EASE® In Situ Applications, Application Note, 2009, 3 pages.
Gdanski et al., "A New Model for Matching Fracturing Fluid Flowback Composition," SPE Hydraulic Fracturing Technology Conference held in College Station, Texas, SPE 106040, Jan. 29-31, 2007, 9 pages.
Bossard et al., "The Design and fabrication of planar multiband metallodielectric frequency selective surfaces for infrared applications", IEEE Trans. On Antennas and Propagation, v. 50, No. 4, Apr. 2006, 12 pages.
Frey et al., "Temperature-dependent refractive index of silicon and germanium," NASA Goodard Space Flight Center, Greenbelt, MD, 2006, 10 pages.
Zoeller et al., "Substantial progress in optical monitoring by intermittent measurement technique," SPIE, Published in the processing of the OSD, Jena 2005, vol. 5963-13, 9 pages.
Haibach et al., "Precision in multivariate optical computing," Applied Optics, vol. 43, No. 10, Apr. 1, 2004, 11 pages.
Rabady et al., "High-resolution photometric optical monitoring for thin-film deposition," Applied Optics, Optical Society of America, vol. 43, No. 1, Jan. 1, 2004, 6 pages.
Priore et al., "Novel Imaging Systems: Multivariate Optical Computing in the UV-VIS," Department of Chemistry and Biochemistry, University of South Carolina, 2003, 5 pages.
Myrick et al., "A single-element all-optical approach to chemometric prediction," Vibrational Spectroscopy 28, 2002, 9 pages.
Myrick, "Multivariate optical elements simplify spectroscopy," Laser Focus World, Mar. 1, 2002, access date Feb. 28, 2013, 3 pages http://www.laserfocusworld.com/articles/print/volume-38/issue-3/features/spectroscopy/multivariate-optical-elements-simplify-spectroscopy.html.
Myrick et al., "Application of multivariate optical computing to simple near-infrared point measurements," SPIE vol. 4574, Department of Chemistry and biochemistry, University of South Carolina, 2002, 8 pages.
Morton et al., "Optical Monitoring of Thin-films Using Spectroscopic Ellipsometry," Society of Vacuum Coaters, 45th Annual Technical Conference Proceedings, 2002, 7 pages.
Paul et al., "Fabrication of mid-infrared frequency-selective surfaces by soft lithography", Applied Optics, v. 40, No. 25, Sep. 2001, 5 pages.
Myrick et al., "Spectral Tolerance Determination for Multivariate Optical Element Design,"Fresenuis' Journal of Analytical Chemistry, 369, 2001, 5 pages.
Eastwood et al., "Filed applications of stand-off sensing using visible/NIR multivariate optical computing," Department of Chemistry and Biochemistry, University of South Carolina, SPE vol. 4199, 2001, 10 pages.
Soyemi et al., "Novel Filter Design Algorithm for Multivariate Optical Computing," Advanced Environmental and Chemical Sensing Technology, SPIE vol. 4205, 2001, 12 pages.
Munk, "Frequency Selective Surfaces: Theory and Design", John Wiley and Sons, Inc., New York, 2000, 92 pages.
Woollam et al., "Overview of Variable Angle Spectroscopic Ellipsometer (VASE), Part 1: Basic Theory and Typical Applications," Society of Photo-Optical Instrumentation Engineers, Critical Reviews of Optical Science Technology CR72, 1999, 28 pages.
Wu, "Frequency Selective Surface and Grid Array", TRW Electronic Systems and Technology Division, John Wiley & Sons, Inc., New York, 1995, 10 pages.
Nelson et al., "Multivariate Optical Computation for Predictive Spectroscopy", Analytical Chemistry 1998, 70, 10 pages.
Grader et al., "Fourier transform infrared spectroscopy of a single aerosol particle," J. Chem. Phys. 86 (11), Jun. 1, 1987, 7 pages.
Li, "Refractive Index of Silicon and Germanium and Its Wavelength and Temperature Derivatives," Center for Information and Numerical Data Analysis and Synthesis, Purdue University, J. Phys. Chem. Ref. Data, vol. 9, No. 3, 1980, 98 pages.

* cited by examiner

INTEGRATED COMPUTATIONAL ELEMENTS WITH FREQUENCY SELECTIVE SURFACE

BACKGROUND

The subject matter of this disclosure is generally related to optical analysis systems for analyzing a substance of interest, for example, crude petroleum, gas, water, or other wellbore fluids. For instance, the disclosed optical analysis systems use an integrated computational element (ICE) that has a frequency selective surface.

Information about a substance can be derived through the interaction of light from the ultraviolet (UV) to infrared (IR) ranges with that substance. The interaction changes characteristics of the light, specifically the frequency (color), intensity, polarization, and/or direction (e.g., through scattering, absorption or refraction). Chemical or physical properties of the substance can be determined based on the changes in the characteristics of the light interacting with the substance. For example, in certain applications, one or more properties of crude petroleum, gas, water, or other wellbore fluids can be derived in-situ in petroleum fields, more commonly referred to as oil fields, as a result of the interaction between these substances and light. For example, downhole instruments can use the interaction between light and substances found downhole for making fluid (oil, gas and water) and geological chemical and physical measurements at well sites.

Integrated computational elements (ICEs) are filters that transform light into chemical or physical information through the use of regression techniques. ICE filters (or simply ICEs) represent pattern recognition systems which recognize certain spectral patterns using vector regression techniques. Typically, an ICE is a substrate with multiple stacked dielectric layers (e.g., about 30 to 50 layers), each having a different refractive index from its adjacent layers. The ICE is configured to selectively pass predetermined fractions of light of different wavelengths. For instance, the number of layers N, the materials and the spacings of the N layers that compose the ICE are selected, e.g., using conventional methods for designing so called optical interference filters, so each wavelength of the light transmitted through the ICE can be weighted in a predetermined manner.

Because ICEs are configured to extract information from light modified by a sample without having to perform spectral analysis outside of the ICEs, they can be incorporated in low cost and rugged instruments. Hence, such ICE-based downhole instruments can provide a relatively low cost, rugged and accurate system for monitoring petroleum quality.

DESCRIPTION OF DRAWINGS

Like reference symbols in the various drawings indicate like elements.

DETAILED DESCRIPTION

Figure 1:
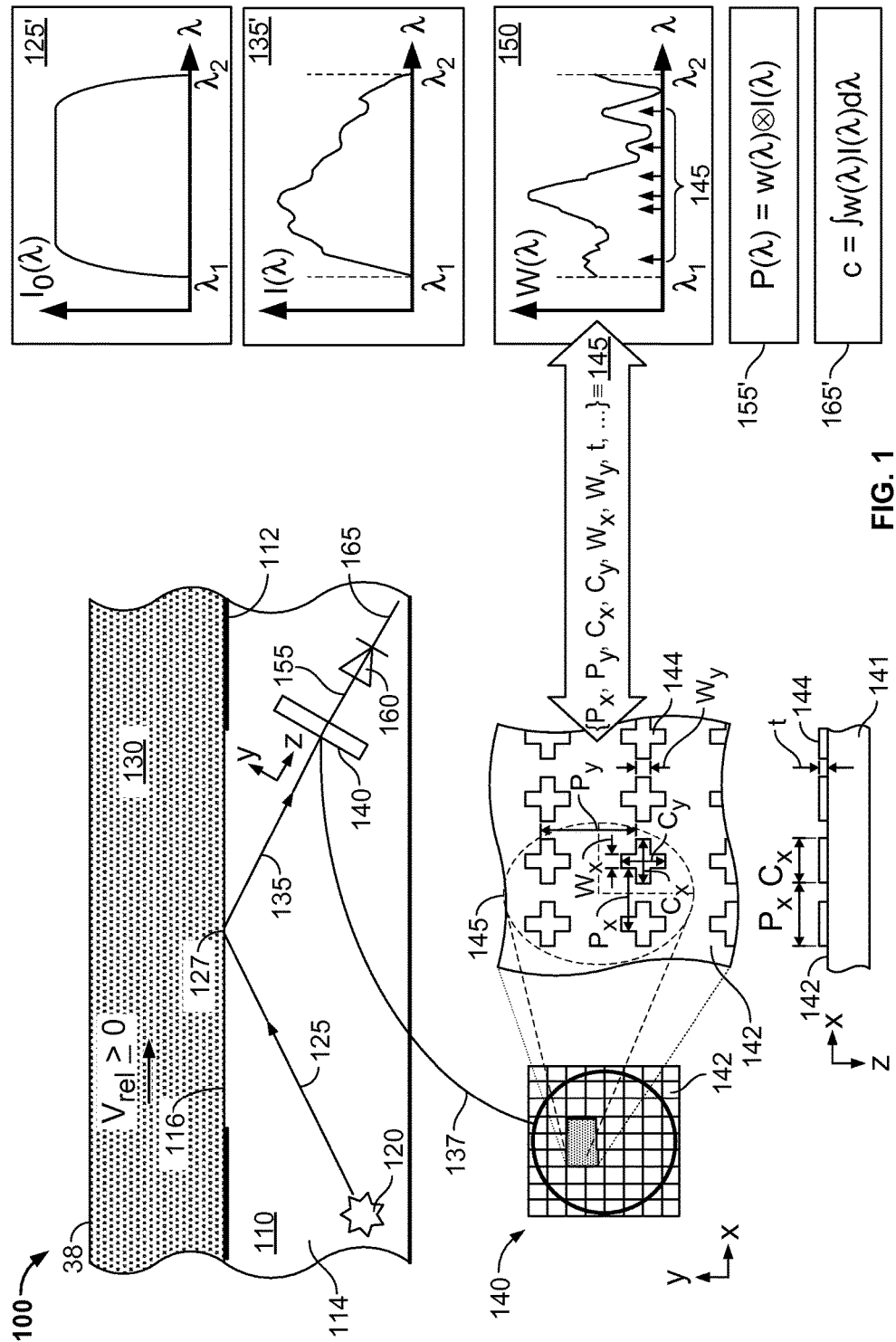
FIG. 1 shows an example of a system for measuring a property of a sample using an ICE that has a frequency selective surface.

Technologies disclosed herein can be used to provide optical analysis systems using an ICE that has a surface patterned to selectively reflect or transmit different wavelengths by different amounts across a spectrum of wavelengths. Such a surface is referred to as a "frequency selective surface" (FSS). In general, there are two categories of FSS. On one hand, a capacitive FSS is a periodic array of conducting patches deposited on a transparent substrate. On the other hand, an inductive FSS is a periodic array of apertures in a conductive layer. In some implementations, the inductive FSS can be a free standing mesh. Note that, for an inductive FSS that operates in the optical range of wavelengths, a perforated conductive layer may be too thin and fragile to be free standing, so in such case, the perforated conductive layer is supported on a transparent substrate. The optical properties (reflectivity, transmissivity, absorptivity, polarization dependence, angular dependence, etc.) of an FSS are primarily dependent on the physical shape and dimensions of the periodic array of conductive patches (or array of apertures in the conductive layer) and the refractive index of the substrate upon which the array is deposited. The conductive (usually metallic) species used in an FSS normally has only second order effects on its optical properties. The conductive patterns making up the FSS can be quite complicated, often blurring the distinction between a capacitive and an inductive FSS. For example, holes or apertures can be formed in the periodic conducting patches. As another example, isolated conducting islands or patches can be disposed in the periodic array of holes formed in the conducting layer. The disclosed optical analysis systems that utilize an FSS-based ICE can be used for measuring one or more properties of various samples, e.g., crude petroleum, gas, water, or other wellbore fluids.

One aspect of the subject matter described in this specification can be implemented in a system that includes a light source that illuminates, during operation of the system, a sample with light having a source spectrum over a wavelength range to obtain light modified by the sample. The light modified by the sample has a modified spectrum over the wavelength range, such that the modified spectrum corresponds to the sample. The system further includes an integrated computational element (ICE) including a substrate and a layer disposed on a surface of the substrate as a frequency-selective surface pattern. The frequency-selective surface pattern is defined in terms of a set of parameters to be spectrally equivalent to a filter spectrum over the wavelength range. The filter spectrum corresponds to a set of spectra of the sample respectively taken for known values of a property of the sample. Moreover, the ICE (i) is arranged to receive the light modified by the sample and (ii) outputs processed light that has a processed spectrum over the wavelength range. Additionally, the system includes a photodetector optically coupled with the ICE to receive the processed light. The photodetector integrates the processed spectrum over the wavelength range to determine a current value of the property of the sample.

Implementations can include one or more of the following features. In some implementations, the set of parameters can include one or more of dimensions of lateral features of the frequency-selective surface pattern, thickness of the layer, material of the layer and material of the substrate on which the layer is disposed. In some cases, the set of parameters further include one or more arrangements of the lateral features of the frequency-selective surface pattern, the arrangements having triangular, rectangular, hexagonal or circular symmetry. Values of the dimensions of the lateral features respectively correspond to spectral features of the filter spectrum. For example, values of the set of parameters determine the wavelength range of the spectral features of the filter spectrum to be from 0.2 to 100 µm. In some cases, first dimensions from among the dimensions of the lateral features respectively correspond to first spectral features of the filter spectrum associated with a first polarization component of the light modified by the sample, and second dimensions from among the dimensions of the lateral features that are orthogonal on and have different values from values of the first dimensions respectively correspond to second spectral features of a second filter spectrum associated with a second, orthogonal polarization component of the light modified by the sample. Here, the second filter spectrum can correspond to a second set of spectra of the sample respectively taken for known values of a second property.

In some implementations, the frequency-selective surface pattern can be laterally periodic over a predetermined portion of the surface of the substrate. For instance, the frequency-selective surface pattern can include a periodic array of conductive patches, such that inside the conductive patches there are one or more apertures. Alternatively or additionally, the frequency-selective surface pattern can include a conductive layer with an array of apertures therein, such that inside the apertures there are one or more conducting patches.

In some implementations, the layer can be disposed on the surface of the substrate as the frequency-selective surface pattern and one or more additional frequency-selective surface patterns. Each of the additional frequency-selective surface patterns is defined in terms of an associated set of parameters to be spectrally equivalent to an associated filter spectrum over the wavelength range, such that the associated filter spectrum corresponds to an associated set of spectra of the sample respectively taken for known values of an additional associated property. Additionally, each of the additional frequency-selective surface patterns is laterally periodic over an associated other predetermined portion of the surface of the substrate, such that other predetermined portions of the surface of the substrate corresponding to the respective additional frequency-selective surface patterns are laterally separated, from each other and from the predetermined portion corresponding to the frequency-selective surface pattern, by separations at least a size of a spot size when the light modified by the sample is received at the ICE.

In some implementations, when the light modified by the sample is received at the ICE, a spot size can encompass at least a threshold quantity of repetitions of the frequency-selective surface pattern. For example, the threshold quantity of repetitions of the frequency-selective surface pattern is about 25 repetitions.

Another aspect of the subject matter described in this specification can be implemented in a measurement tool that includes an optical element including a layer of material patterned so that the optical element selectively transmits or reflects, during operation of the measurement tool, light in at least a portion of a wavelength range by differing amounts, the differing amounts being related to a property of a sample.

Implementations can include one or more of the following features. In some implementations, the wavelength range can include wavelengths in a range from about 0.2 µm to about 25 µm. In some implementations, the sample can include wellbore fluids and the property of the sample is a property of the wellbore fluids. For example, the property of the sample is selected from among a concentration of a substance in the sample, a pH of the sample, a ratio of concentrations of two different substances in the sample, a density of the sample, and a viscosity of the sample.

In some implementations, the optical element can include a substrate supporting the layer of patterned material and the layer of patterned material includes a plurality of identical features arranged in an array on a first surface of the substrate. The features each can include one or more geometric shapes selected from the group consisting of triangles, quadrilaterals, hexagons, and circles.

In some implementations, the optical element can include another layer of patterned material supported on a second surface of the substrate opposing the first surface. The other layer of patterned material includes a plurality of identical other features arranged in another array on the second surface. Here, the optical element selectively transmits or reflects light by differing amounts in (i) a first portion of the wavelength range in accordance with the array of the identical features of the layer of patterned material supported on the first surface, and (ii) a second portion of the wavelength range in accordance with the other array of the identical other features of the other layer of patterned material supported on the second surface.

In some implementations, the substrate of the optical element can include a dielectric interference filter. Here, the optical element selectively transmits or reflects light by differing amounts in (i) a first portion of the wavelength range in accordance with the array of the identical features of the layer of patterned material, and (ii) a second portion of the wavelength range in accordance with the dielectric interference filter. In some cases, the optical element can include another layer of patterned material supported on a second surface of the substrate opposing the first surface. The other layer of patterned material includes a plurality of identical other features arranged in another array on the second surface. In the latter cases, the optical element selectively transmits or reflects light by differing amounts in (i) the first portion of the wavelength range, (ii) the second portion of the wavelength range, and (iii) a third portion of the wavelength range in accordance with the other array of the identical other features of the other layer of patterned material supported on the second surface.

In some implementations, the measurement tool can include a light source positioned to illuminate the sample with light having a first spectrum over the wavelength range. Moreover, the optical element can be positioned to receive light from the sample in response to the illumination, such that the light received from the sample has a second spectrum over the wavelength range. The second spectrum corresponds to the first spectrum modified by the sample. Further, the measurement tool can include a detector positioned to receive light from the optical element and produce a signal having a value related to an integrated intensity of the light from the optical element across the wavelength range. The signal value corresponds to a value of the property of the sample. Furthermore, the measurement tool can include a transparent element positioned in a path of the light between the light source and the sample. Here, the optical element is positioned to receive light reflected from an interface between the sample and the transparent element.

In another aspect, a method can include placing the foregoing measurement tool in a wellbore, and determining the value of a property of a sample in the wellbore using the placed measurement tool.

One or more of the following advantages can be realized. Processes used to fabricate the disclosed ICEs with frequency selective surface may be less complex than the processes used to fabricate conventional ICEs. The processes used to fabricate conventional ICEs typically include thin film deposition techniques such as sputtering, chemical vapor deposition, atomic layer deposition for depositing N>30 layers included in conventional thin film based ICEs. During such deposition processes, as the actual thickness deposited for each layer may deviate from the original design due to possible variations in the environment as well as in control, it is necessary to continuously monitor the film growth, and run a complex optimization algorithm in real time to ensure that each of the finished films is as close to the original design as possible. Once the conventional thin film based ICEs are deposited successfully, they are subject to a thermal annealing process in order to ensure that they can properly function at elevated temperatures.

In contrast, the disclosed ICEs with frequency selective surface may be fabricated using conventional photolithography techniques to form the patterned layer. Such conventional photolithography techniques enable (i) large-scale production of inexpensive and reliable ICEs with frequency selective surface; (ii) reduction/elimination of high cost vacuum deposition chambers and controls; (iii) elimination of the real-time optimization procedure currently required when depositing conventional thin film based ICEs. As such, significant cost reduction and increase in quality/reliability can be achieved when fabricating ICEs with frequency selective surface because they are simpler to fabricate compared to the conventional thin film based ICEs.

Further, the disclosed ICEs with frequency selective surface can be calibrated at design-level (e.g., once over several/all batches) in contrast with the conventional ICEs which generally require batch-level calibration (e.g., batch-to-batch calibration). Before conventional ICEs can be used in a tool, they are calibrated with known fluid standards, at different temperatures and pressures. The calibration process minimizes adverse effects caused by unavoidable differences, even in ICEs of identical design, induced by the above-noted complex fabrication process. The conventional photolithography techniques used to fabricate the ICEs with frequency selective surface enable reduction in the amount of time and effort required for calibration, since frequency selective surface patterns can be fabricated to have better uniformity and fewer variations from batch to batch compared to the multilayered structures of the conventional ICEs.

In general, ICEs with frequency selective surface contain a single reflective layer on a bulk substrate and, hence, they may be more robust and/or have higher transmission of light when compared to conventional ICEs which typically contain more than 30 layers of two different materials. In view of the above reasons, measurement tools that use ICEs with frequency selective surface have lower cost in manufacture, calibration and maintenance compared to measurement tools that use conventional thin film based ICEs.

Additionally, the disclosed ICEs may be inherently better suited for operation in the mid to far-IR spectral ranges than the conventional ICEs, which are mostly used in the near-IR spectral range. Conventional ICEs include multiple interlaced layers of two materials with different indices of refraction. Combinations of the number of layers, thickness thereof, and properties of the conventionally used materials enable design of conventional ICEs with a filter spectrum that extends into the near-IR spectral range. In contrast, a filter spectrum of ICEs with frequency selective surface can extend to mid-IR or far-IR because a frequency selective surface pattern equivalent to such a mid/far-IR filter spectrum can be designed by an appropriate choice of corresponding lateral dimensions of elements of the frequency selective surface pattern.

Accordingly, an ICE with a filter spectrum that extends from the UV-vis to the mid-IR or far-IR can be obtained either by fabricating an FSS on a support substrate, such that the FSS is spectrally equivalent to a filter spectrum of the ICE that extends over the desired spectral range; or by fabricating an FSS on a conventional ICE, such that a filter spectrum of the resultant ICE is composed from a filter spectrum of the conventional ICE, e.g., over the UV-vis to near-IR spectral range, augmented by an extended filter spectrum, e.g., over the mid-IR or far-IR, to which the FSS is equivalent.

Details of one or more of the foregoing embodiments are described below.

FIG. 1A shows aspects of an example of a system 100 for measuring one or more properties of a sample using an ICE that has a frequency selective surface. The system 100 includes a measurement tool 110 optically coupled to a sample 130. In this example, the sample 130 can be crude petroleum, gas, water, or other wellbore fluids contained in a pipe 38 that can be part of a pipeline or a downhole pipe in a well. The downhole pipe may be a vertical pipe or horizontal pipe and may be part of a well head, a pipeline, or a well completion. Pipe 38 may be internal to a sampler, or other downhole sensing tool. In some implementations, a window 116 separates the measurement tool 110 from the sample 130, such that sensors inside the measurement tool 110 measure attributes of fluids surrounding the measurement tool 110. In some implementations, the pipe 38 can be a flow line in a wireline or logging while drilling formation pump out tester where formation fluid is drawn into the measurement tool 110 and analyzed in order to characterize a reservoir. In some cases, the sample 130 can be relatively at rest with respect to the measurement tool 110 ($V_{rel}=0$) during the measurement, for example when both the measurement tool 110 and fluid in the pipe 38 move at the same velocity or are both stationary. In some other cases, the measurement tool 110 can move relative to the sample 130 ($|V_{rel}|>0$) during the measurement, for example when the measurement tool 110 is pushed/pulled through stationary fluid in the pipe 38, or when the fluid flows through the pipe 38 with a flow velocity different from the velocity of the measurement tool 110.

In this example, the measurement tool 110 includes a light source 120, an ICE 140 that has a frequency selective surface, and a photodetector 160. The measurement tool 110 has a frame 112 such that these components are arranged in an enclosure 114 thereof. A cross-section of the measurement tool 110 in a plane perpendicular to the page can vary, depending on the space available. For example, the measurement tools' cross-section can be circular or rectangular, for instance. The measurement tool 110 directs light to the sample 130 through an optical interface 116, e.g., an aperture/window in the frame 112. The measurement tool 110 is configured to probe the sample 130 (e.g., the wellbore fluids flowing) in the pipe 38 through the optical interface 116 and to determine an amount (e.g., a value) of a given property (also referred to as a property to be measured) of the probed sample 130. The property to be measured can be any one of multiple properties of the sample 130 including concentration of a given substance in the sample, a gas-oil-ratio (GOR), pH value, density, viscosity, etc.

The light source 120 outputs light having a source spectrum $I_0(\lambda)$ 125' over a particular wavelength range, from a first wavelength $\lambda_1$ to a second wavelength $\lambda_2$. In some implementations, the source spectrum 125' can have non-zero intensity over the entire or most of the wavelength range $\lambda_2$-$\lambda_1$. In some implementations, the source spectrum 125' extends through UV-vis (0.2-0.8 µm) and near-IR (0.8-2.5 µm) spectral ranges. Alternatively, or additionally, the source spectrum 125' extends through near-IR and mid-IR (2.5-25 µm) spectral ranges. In some implementations, the source spectrum 125' extends through near-IR, mid-IR and far-IR (25-100 µm) spectral ranges. In some implementations, the light source 120 is tunable and is configured in combination with time resolved signal detection and processing.

The example of source spectrum 125' illustrated in FIG. 1 is depicted as being substantially flat over most of the noted wavelength range, however, in general, the intensity at different wavelengths across the spectral band of interest may vary.

The light source 120 is arranged to direct a probe beam 125 of the source light towards the optical interface 116 where it illuminates the sample 130 at a location 127. The source light in the probe beam 125 interacts with the sample 130 and reflects off it as light modified by the sample 130. The light modified by the sample has a modified spectrum $I(\lambda)$ 135' over the particular wavelength range. In the reflective configuration of the measurement tool 110 illustrated in FIG. 1 (i.e., where the light to be analyzed reflects at the sample/window interface), the modified spectrum $I(\lambda)$ 135' is a reflection spectrum associated with the sample 130. In a transmission configuration of the measurement tool 110 (not shown in FIG. 1), the probe beam is transmitted through the sample as modified light, such that the modified spectrum is a transmission spectrum associated with the sample. Examples of modified spectra $I(\lambda)$ 135' are described below in connection with FIG. 7. In general, the modified spectrum $I(\lambda)$ 135' encodes information about multiple properties associated with the sample 130, and more specifically the encoded information relates to current values of the multiple properties.

With continued reference to FIG. 1, and the Cartesian coordinate system provided therein for reference, the ICE 140 is arranged to receive a beam 135 of the modified light, and is configured to process it and to output a beam 155 of processed light. The beam 135 of modified light is incident on a first surface 142 of the ICE 140 along the z-axis, and the beam 155 of processed light is output along the z-axis after transmission through the ICE 140. Alternatively or additionally, the beam 155 (or an additional reflected beam) of processed light can be output after reflection off the first surface 142 of the ICE 140. The ICE 140 is configured to process the modified light by filtering it in accordance with a filter spectrum $w(\lambda)$ 150 associated with a property to be measured.

The filter spectrum $w(\lambda)$ 150 is determined offline by applying conventional processes to a set of modified spectra $I(\lambda)$ of the sample which correspond to respective known values of the property to be measured. For instance, a filter spectrum $w(\lambda)$ can be determined through regression analysis of N modified spectra $I_j(\lambda)$ of a sample, where j=1−N, such that each of the modified spectra $I_j(\lambda)$ corresponds to an associated known value of a given property for the sample. The regression analysis detects, within the N modified spectra $I_j(\lambda)$, the filter spectrum $w(\lambda)$ that is unique to identifying and quantifying the given property. In this manner, when a value of the given property for the sample is unknown, a modified spectrum $I_u(\lambda)$ of the sample can be acquired and then parsed with the ICE 140 to determine a magnitude of the filter spectrum $w(\lambda)$ within the modified spectrum $I_u(\lambda)$. The determined magnitude represents the unknown value of the given property for the sample.

For example, the sample 130 can be a compound containing substances X, Y and Z, and the property to be measured for the sample 130 is concentration $c_X$ of substance X in the compound. In this case, N modified spectra $I_j(\lambda)$ were acquired for N samples of the compound having respectively known concentration values for each of the substances contained in the N samples. By applying regression analysis to the N modified spectra $I_j(\lambda)$, a filter spectrum $w_{cX}(\lambda)$ that is unique for the concentration $c_X$ of the X substance can be detected (recognized). Similarly, filter spectra $w_{cY}(\lambda)$ and $w_{cZ}(\lambda)$ that are respectively unique for concentrations $c_Y$ and $c_Z$ of the Y and Z substances can also be detected. In this manner, when a new sample 130 of the compound has an unknown concentration $c_X$ of the X substance, for instance, a modified spectrum $I_n(\lambda)$ of the new sample 130 can be acquired and then parsed to determine a magnitude of the filter spectrum $w_{cX}(\lambda)$ within the modified spectrum. The determined magnitude represents the unknown value of the concentration $c_X$ of the X substance for the new sample 130.

In the example illustrated in FIG. 1, the ICE 140 includes a substrate 141 having a first surface 142, and a conductive layer 144 disposed on the first surface 142 of the substrate forming a frequency-selective surface with periodic structures 145. In this case, the periodic structures 145 are formed from conductive patches. The periodic structures 145 of the FSS are also referred to, interchangeably, as an FSS pattern 145. Features of the periodic structures 145 of the FSS are defined, in terms of a set of parameters, to render the FSS pattern 145 spectrally equivalent to the filter spectrum $w(\lambda)$ 150 associated with the property to be measured, as described in detail below. In this manner, the beam 155 of processed light output by the ICE 140 has a processed spectrum $P(\lambda)=w(\lambda) \otimes I(\lambda)$ 155' over the wavelength range $\lambda_2$-$\lambda_1$, such that the processed spectrum 155' represents the modified spectrum $I(\lambda)$ 135' weighted by the filter spectrum $w(\lambda)$ 150 associated with the property to be measured.

The beam 155 of processed light is directed from the ICE 140 to the photodetector 160, which detects the processed light and outputs a detector signal 165. A value (e.g., a voltage) of the detector signal 165 is a result of an integration of the processed spectrum 155' over the particular wavelength range and corresponds to the unknown value "c" 165' of the property to be measured for the sample 130. If the ICE 140 (or a second ICE—not shown in FIG. 1) contained a second FSS pattern defined to be spectrally equivalent to a second filter spectrum $w_2(\lambda)$ associated with a second property of the sample 130, a second processed spectrum would represent the modified spectrum $I(\lambda)$ 135' weighted by the second filter spectrum $w_2(\lambda)$, such that a second value of a second detector signal corresponds to a value of the second property for the sample 130. In some implementations, the determined value 165' of the property to be measured can be logged along with a measurement time, geo-location, and other metadata, for instance. In some implementations, the detector signal 165, which corresponds to a property to be measured by the measurement tool 110, can be used as a feedback signal to adjust the property of the sample, to modify the sample or environmental conditions associated with the sample, as desired.

Various implementations of an ICE 140 containing a frequency selective surface are now described. In the example illustrated in FIG. 1, the first surface 142 is oriented along the x-y plane of the Cartesian coordinate system local to the ICE 140. The set of parameters, which render the FSS pattern 145 spectrally equivalent to the filter spectrum $w(\lambda)$ 150 associated with the property to be measured, includes one or more of dimensions of lateral features of the FSS pattern 145, thickness "t" of the layer 144, material of the conducting layer 144 and material of the substrate 141 on which the layer 144 is deposited. In addition, the set of parameters further includes one or more arrangements of the lateral features of the FSS pattern 145. Such arrangements can have a variety of geometric shapes, such as triangular, rectangular, hexagonal or circular, as described in detail below. The FSS pattern 145 associated with the ICE 140 represents an example of a capacitive FSS.

The substrate 141 can be fabricated from a material that is transparent over the wavelength range $\lambda_2-\lambda_1$. The substrate material can be diamond, Ge, ZnSe (or other transparent dielectric material), and can have a thickness in the range of 0.02-2 mm, for instance, to insure structural integrity of the ICE 140. There is no upper limit for the substrate thickness from the stand point of filtering characteristics of the ICE 140. The layer 144 is a metal layer that reflects the incident beam 135 of the modified light. An efficient FSS has a thickness "t" of the metal layer 144 of at least three skin depths. A skin depth is the distance (measured from the surface) into the metal layer 144 where the incident electric (or magnetic) field of the incident beam 135 drops by a factor of 1/e. The skin depth depends on the metal species (Al, Au, Ag, etc.) and on the wavelength of the incident beam 135. In this manner, the thickness of the metal layer 144 can be in the range of 0.05 to 2 μm, for instance.

In the example illustrated in FIG. 1, the structures 145 of the frequency-selective surface include a periodic array of cross-shaped conducting patches. In this example, the cross-arm along the x-axis has length $c_x$ and a width $w_x$, while a second cross-arm along the y-axis has length $c_y$ and a width $w_y$. The lengths of the two cross-arms of the crosses can be equal, $c_x=c_y$, or different, $c_x \neq c_y$. Moreover, the widths of the two cross-arms of the crosses can be equal, $w_x=w_y$, or different, $w_x \neq w_y$. Additionally, the crosses of the FSS pattern 145 are separated from each other along the x-axis by a period $p_x$ and along the y-axis by a period $p_y$. The lateral separations of the crosses along the x and y-axes can be equal, $p_x=p_y$, or different, $p_x \neq p_y$. If all the corresponding x and y parameters for the crosses shown in FIG. 1 are equal, e.g., $c_x=c_y$, $w_x=w_y$, and $p_x=p_y$, the spectral properties of the FSS are polarization independent. On the other hand, if one or more of the corresponding x and y parameters are not equal, the spectral properties of the FSS depend on the state of polarization of the incident modified beam 135, as described in detail below.

In general, values of the dimensions of the lateral features, $p_x$, $p_y$, $c_x$, $c_y$, $w_x$, $w_y$, and combinations thereof $p_x \pm c_x$, $p_x \pm w_x$, $c_x \pm w_x$, $p_y \pm c_y$, . . . determine primary spectral features (e.g., spectral location of peaks, shoulders, etc.) of the filter spectrum $w(\lambda)$ 150. For example, a single cross of the FSS pattern 145 corresponds to a resonance for y polarization of approximately $2c_y \cdot \sqrt{((n_1^2+n_2^2)/2)}$, where $n_1$ is the refractive index of the material where the incident light is coming from and $n_2$ is the refractive index of the substrate 141. In the example illustrated in FIG. 1, the resonance is reflective because the FSS pattern 145 is formed from conductive patches (and thus, the frequency-selective surface is a capacitive FSS). In the example illustrated in FIGS. 2A-2B, the resonance is transmissive because the FSS pattern 245 is formed from apertures in a conductive layer (and thus, the frequency-selective surface is an inductive FSS). Referring again to FIG. 1, values of the metal thickness, and properties of the materials of the layer 140 and of the substrate 141 contribute to secondary spectral features (e.g., height, width, shape of peaks, shoulders, etc.) of the filter spectrum $w(\lambda)$ 150.

Additionally, a frequency-selective surface of the ICE 140 has a periodic structure, and thus, the FSS exhibits diffraction for wavelengths less than the diffraction limit, e.g., $p_y \cdot \max(n_1, n_2)$ for the FSS pattern 145 and y polarization. Accordingly, an ICE 140 with a frequency-selective surface should be used at wavelengths in excess of the diffraction limit corresponding to the associated periodic structure.

In some implementations, the FSS pattern 145 can be configured to be spectrally equivalent to (i) a first filter spectrum $w(\lambda)$ 150 as the ICE 140 processes a first polarization component $I_1(\lambda)$ (e.g., along the x-axis) of the modified spectrum 135', and (ii) a second filter spectrum $w_2(\lambda)$ (not shown in FIG. 1) as the ICE 140 processes a second, orthogonal polarization component $I_2(\lambda)$ (e.g., along the y-axis) of the modified spectrum 135'. Such birefringent configuration of the ICE 140 can be obtained when (i) first dimensions, e.g., $p_x$, $c_x$, and/or $w_x$, from among the dimensions of the lateral features respectively correspond to first spectral features of the first filter spectrum $w(\lambda)$ 150 associated with the first polarization component of the modified spectrum 135', and second dimensions, e.g., $p_y$, $c_y$, and/or $w_y$, from among the dimensions of the lateral features that are orthogonal on and have different values from values of the first dimensions respectively correspond to second spectral features of the second filter spectrum $w_2(\lambda)$ associated with the second, orthogonal polarization component of the modified spectrum 135'. In this case, the processed spectrum 155' carries two orthogonal, and thus separable, components $P_1(\lambda)=w(\lambda)_1 \otimes I_1(\lambda)$ and $P_2(\lambda)=w_2(\lambda) \otimes I_2(\lambda)$, corresponding to the orthogonal polarizations of the beam 155 of processed light.

A polarizing beam-splitter (not shown in FIG. 1) placed in the path of the beam 155 of processed light can be configured to allow transmission of a first polarization component of the processed spectrum $P_1(\lambda)=w_1(\lambda) \otimes I_1(\lambda)$ towards the photodetector 160, and to redirect a second polarization component of the processed spectrum $P_2(\lambda)=w_2(\lambda) \otimes I_2(\lambda)$ towards a second photodetector (not shown in FIG. 1.) Moreover, the first filter spectrum $w(\lambda)$ 150 can be associated with a first property of the sample 130, and the second filter spectrum $w_2(\lambda)$ can be associated with a second, different property of the sample 130. In this fashion, such birefringent configuration of the ICE 140 would enable the measurement tool 110 to simultaneously obtain (i) an unknown value "c" 165' of the first property from a first detector signal 165 at the photodetector 160: $c_1=\int w_1(\lambda) I_1(\lambda) d\lambda$; and (ii) an unknown value of the second property from a second detector signal at the second photodetector: $c_2=\int w_2(\lambda) I_2(\lambda) d\lambda$.

As disclosed above, the structures 145 of the FSS form a periodic array over the first surface 142 of the substrate in order for the FSS to be spectrally equivalent to the filter spectrum w(λ) associated with the ICE 140. For instance, in the example illustrated in FIG. 1, the FSS pattern 145 is periodic along the x-axis and along the y-axis. Because the measurement tool 110 is configured with a finite (non-infinity) beam size 137, only a finite quantity Nx of columns (distributed along the x-axis) and a finite quantity Ny of rows (distributed along the y-axis) of the periodic array of structures 145 of the FSS, which are inscribed within the beam size 137, contribute to the processing of the modified spectrum 135' by the ICE 140. In this manner, a minimum quantity, $N_{0x}$, of rows and a minimum quantity, $N_{0y}$, of columns of the array of structures 145 should be inscribed within the spot size 137, such that the ICE 140 processes the modified spectrum 135' in accordance with the filter spectrum w(λ) 150. Such minimum quantity, $N_{0x}$, of rows and minimum quantity, $N_{0y}$, of columns of the array of structures 145 to be inscribed within the spot size 137 can be determined empirically for various combinations of shapes, metals, substrates, etc., of an FSS. In some implementations corresponding to the examples of FSS illustrated in FIGS. 1, 2A, 3A and 4A, the minimum quantities of rows and columns of the array of structures 145 of the FSS, which should be inscribed within the spot size 137, such that the ICE processes the modified spectrum in accordance with the filter spectrum w(λ) associated with the ICE, are about $N_{0x} \approx N_{0y} \approx 5$. In this manner, a minimum quantity $N_0$ of structures 145 of the array to be inscribed in the spot size is about $N_0 \approx 25$.

Conversely, the quantity $N > N_0$ of structures 145 chosen to be inscribed within the beam size 137 can be used to establish a diameter of the beam size 137. For instance, in the example illustrated in FIG. 1, N≈64 structures 145 of an FSS with a largest lateral dimension of about 25 µm are chosen to be inscribed within the spot size 137. Accordingly, the diameter of the spot size 137 should be about $2(\sqrt{N/\pi})$ ·(largest lateral dimension)≈2*8×25/($\sqrt{\pi}$)≈225 µm.

In the example illustrated in FIG. 1, an arrangement of the crosses of the FSS pattern 145 is a rectangular arrangement. Structures of a frequency-selective surface other than cross shaped patches and arrangements of the structures having symmetries other than rectangular symmetry are described below.

Figure 2A:
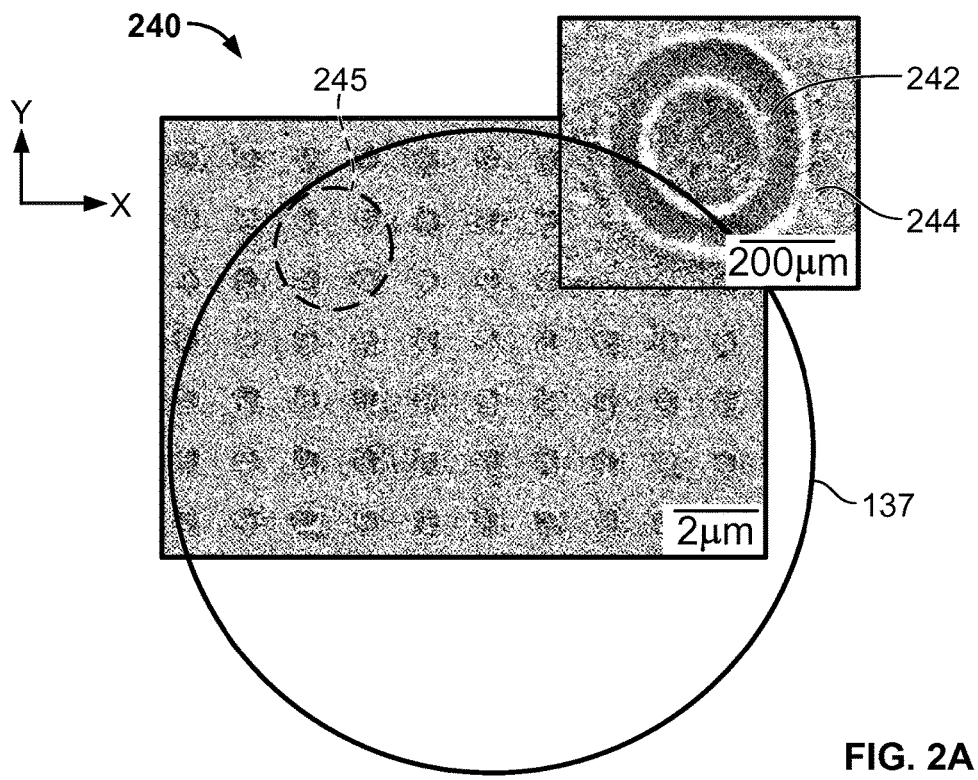
FIGS. 2A-2B show aspects of an example of a frequency-selective surface pattern of an ICE and its equivalent filter spectrum.
Figure 2B:
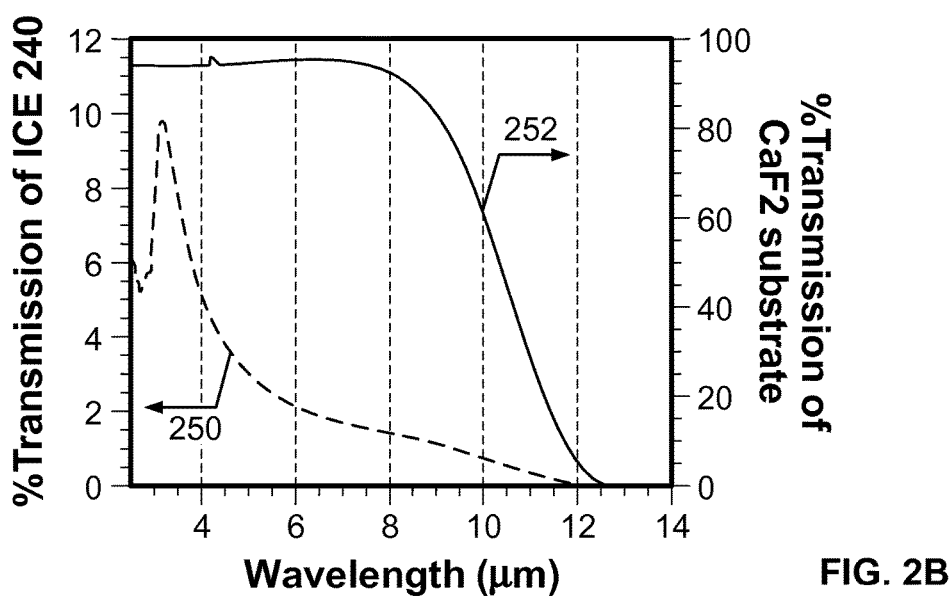

FIGS. 2A-2B show an example of an FSS pattern 245 of an ICE 240 and its equivalent filter spectrum w(λ) 250. The FSS pattern 245 of the ICE 240 can be designed and fabricated using conventional techniques.

FIG. 2A shows that the ICE 240 has an Al layer 244 deposited on a first surface 242 of a CaF$_2$ substrate. The FSS pattern 245 includes rings of an outer diameter approximately 0.7 µm. A width of the trench in the Al layer 244 is about 0.1 µm. The rings of the FSS pattern 245 are separated by 2.3 µm center-to-center. An arrangement of the rings of the FSS pattern 245 has rectangular symmetry. The FSS pattern 245 represents an example of an inductive FSS.

Moreover, the FSS pattern 245 is laterally periodic along the x-axis and along the y-axis over a portion of the first surface 242 of the substrate. A spot size 137 that encompasses N≈80 copies of the FSS pattern 245 is illustrated for reference. Although such a spot size 137 is only about 20 µm wide, a sufficiently large quantity $N > N_0$ of structures 245 are inscribed in the spot size 137, such that the ICE 240 can process a modified spectrum 135' in accordance with an associated filter spectrum filter spectrum w(λ) 250. The associated filter spectrum w(λ) 250 is described below in connection with FIG. 2B. Typically, a measurement tool 110 that includes the ICE 240 is configured such that a spot size of the beam 135 of modified light, when it reaches the first surface 242 of the ICE 240, is larger than the spot size 137 of 20 µm depicted in FIG. 2A.

Moreover, for a first surface 242 of the ICE 240 with lateral dimensions of order ¼" (≈6 mm), multiple different FSS patterns can be deposited, side-by-side, on other portions of the first surface 242. (Not shown in FIG. 2A.) Such frequency-selective surface ICEs that have on the first surface an arrangement of multiple FSS patterns are described in detail below in connection with FIGS. 6A-6B.

FIG. 2B shows a filter spectrum w(λ) 250 equivalent to the FSS pattern 245, and a transmission spectrum 252 of the CaF$_2$ substrate alone. The filter spectrum w(λ) 250 has a mid-IR transmission band at 3.18 µm and a cut-off at 13 µm. The cutoff in transmission of the ICE 240 at 13 µm is due to the corresponding cutoff in transmission of the CaF$_2$ substrate.

Figure 3A:
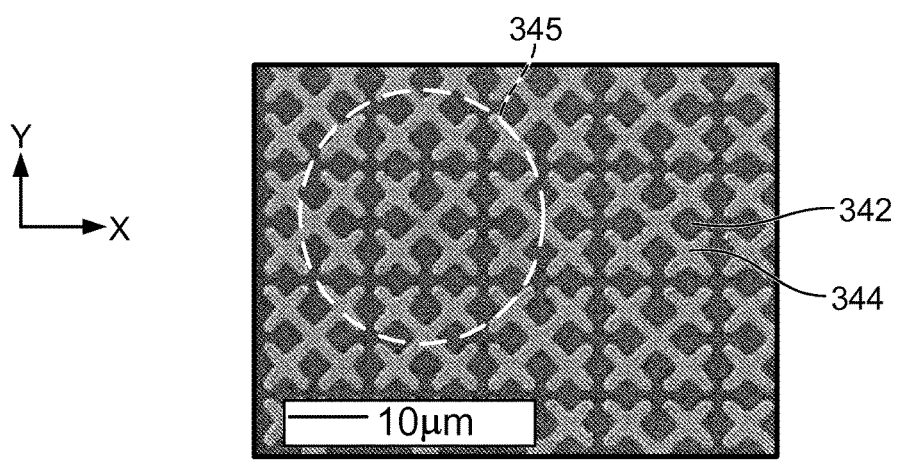
FIGS. 3A-3C show another example of a frequency-selective surface pattern of an ICE and its equivalent filter spectrum.
Figure 3B:
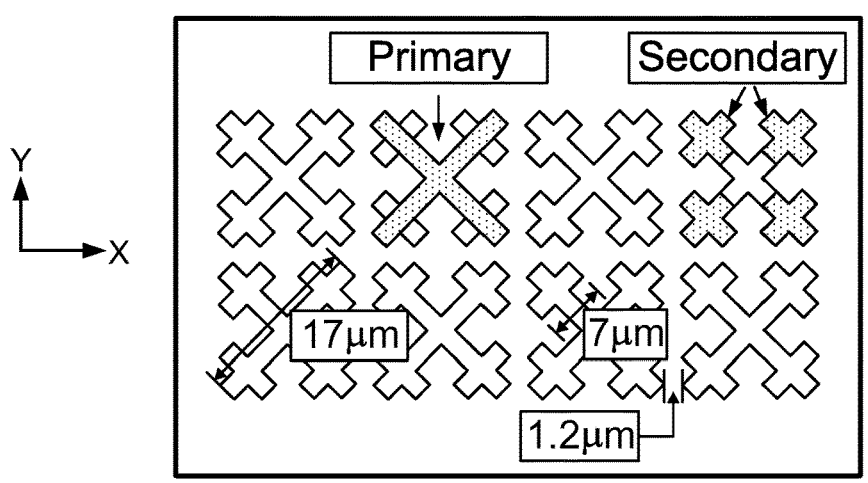
Figure 3C:
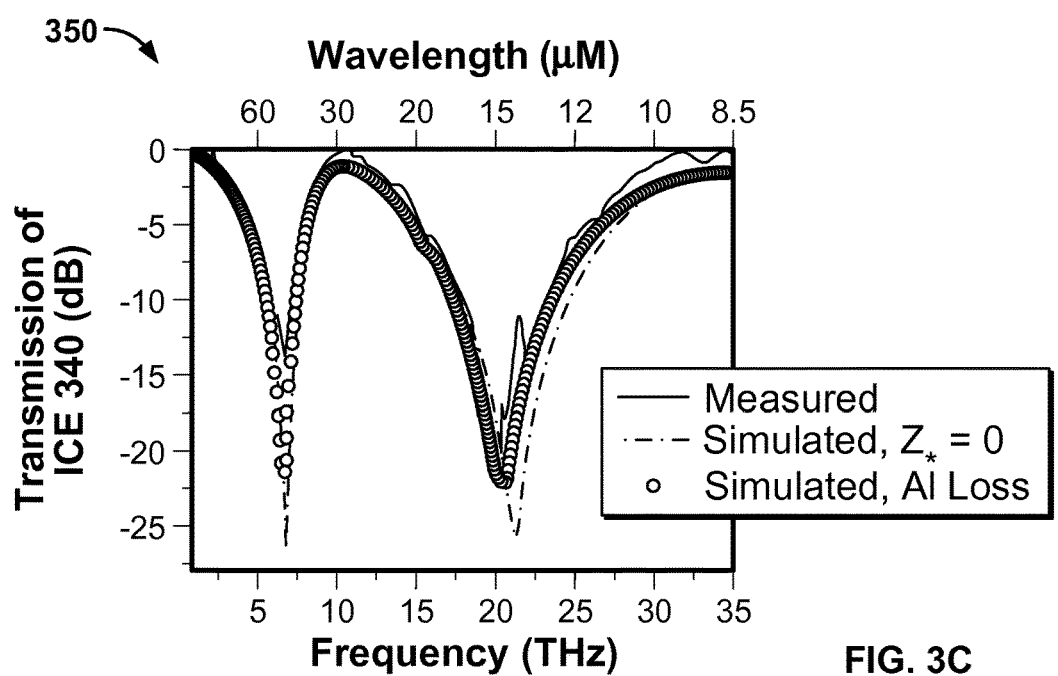

FIGS. 3A-3C show another example of an FSS pattern 345 of an ICE 340 and its equivalent filter spectrum w(λ) 350. The FSS pattern 345 of the ICE 340 can be designed and fabricated using conventional techniques.

FIG. 3A shows that the ICE 340 has an Al layer 344 deposited on a first surface 342 of a polyimide substrate. Polyimide was chosen because it is transmissive in the far-IR. In this case, a thickness of the polyimide substrate was between 0.5-4 µm, and a thickness of the Al layer 344 was 75 nm. The FSS pattern 345 includes fractal cross dipole patches. Moreover, the FSS pattern 345 is laterally periodic along the x-axis and along the y-axis over a portion of the first surface 342 of the substrate. FIG. 3B shows primary cross dipoles with arm lengths of 17 µm, and secondary cross dipoles with arm lengths of 7 µm. A line width of the primary and secondary cross dipoles is 1.5 µm. The spacing between the fractal elements is 1.2 µm which results in a periodic spacing of 12 µm in the horizontal and vertical directions. The FSS pattern 345 represents an example of a capacitive FSS.

FIG. 3C shows a filter spectrum w(λ) 350 equivalent to the FSS pattern 345. In this case, the filter spectrum w(λ) 350 has a mid-IR stop band at 14 µm, which is a resonant wavelength corresponding to the arms of the secondary cross dipoles, and a far-IR stop band at 45 µm, which is a resonant wavelength corresponding to the arms of the primary cross dipoles. Moreover, simulation data including metallic and dielectric losses (represented as circles) is an excellent match to the measured data (represented as solid curve). Additional simulation data (represented by dashed-dotted curve) predicts the response of the ICE 340 with a perfectly conducting Al layer 344 (resistivity=0). Comparing these two simulations indicates that a complex surface impedance model of the Al layer 344 shifts the resonance of the FSS pattern 345 and reduces the filtering performance in the mid-IR and far-IR stop-bands relative to the ideal lossless case.

The foregoing results suggest that both simulations (including and excluding metallic losses) are accurate at longer wavelengths, but diverge at shorter wavelengths. This means that the resistivity of real metals at the longer wavelengths is effectively equal to a perfect conductor. FIG. 3C shows that the crossover wavelength, where taking or not taking into account resistivity of real metals matters, is around 20 micrometers. Since the computational resources required to simulate a perfect conductor are much less than that for a real metal, if a desired FSS filter spectrum has no resonances at wavelengths less than say 15 micrometers or so, a lot of computational resources can be saved in the iterative design of a frequency-selective surface by assuming the metal is a perfect conductor.

Examples of capacitive FSS were described above in connection with FIGS. 1 and 3, and an example of an inductive FSS was described above in connection with FIG. 2. In some implementations, structures of a frequency-selective surface include one or more conducting patches (including but not limited to square, rectangular, circular, elliptical or cruciform shapes) inside periodic apertures in a conducting layer. In some implementations, the structures of the frequency-selective surface include one or more apertures inside periodic conducting patches. In some implementations, the structures of the frequency-selective surface include combinations of both conducting patches inside periodic apertures in the conductive layer and apertures inside periodic conductive patches. Examples of such combinations are described below.

Figure 4A:
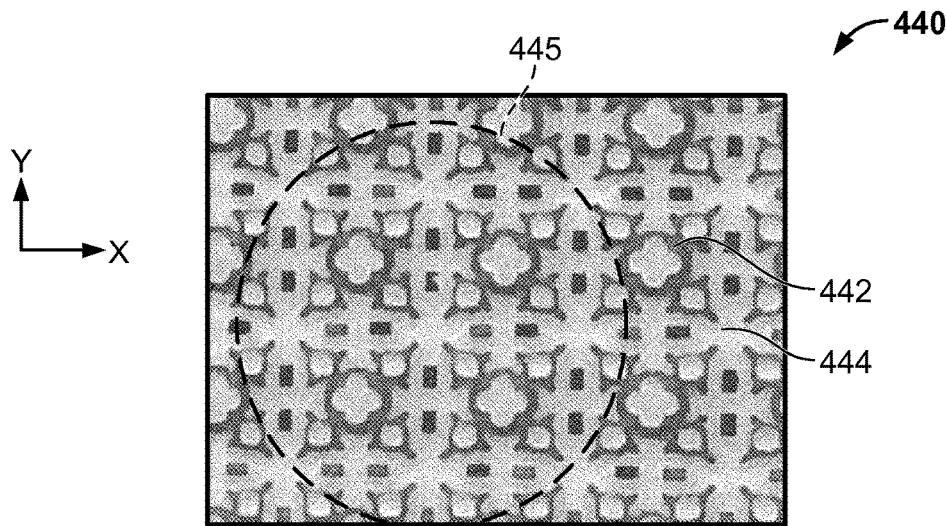
FIGS. 4A-4B show aspects of yet another example of a frequency-selective surface pattern of an ICE and its equivalent filter spectrum.
Figure 4B:
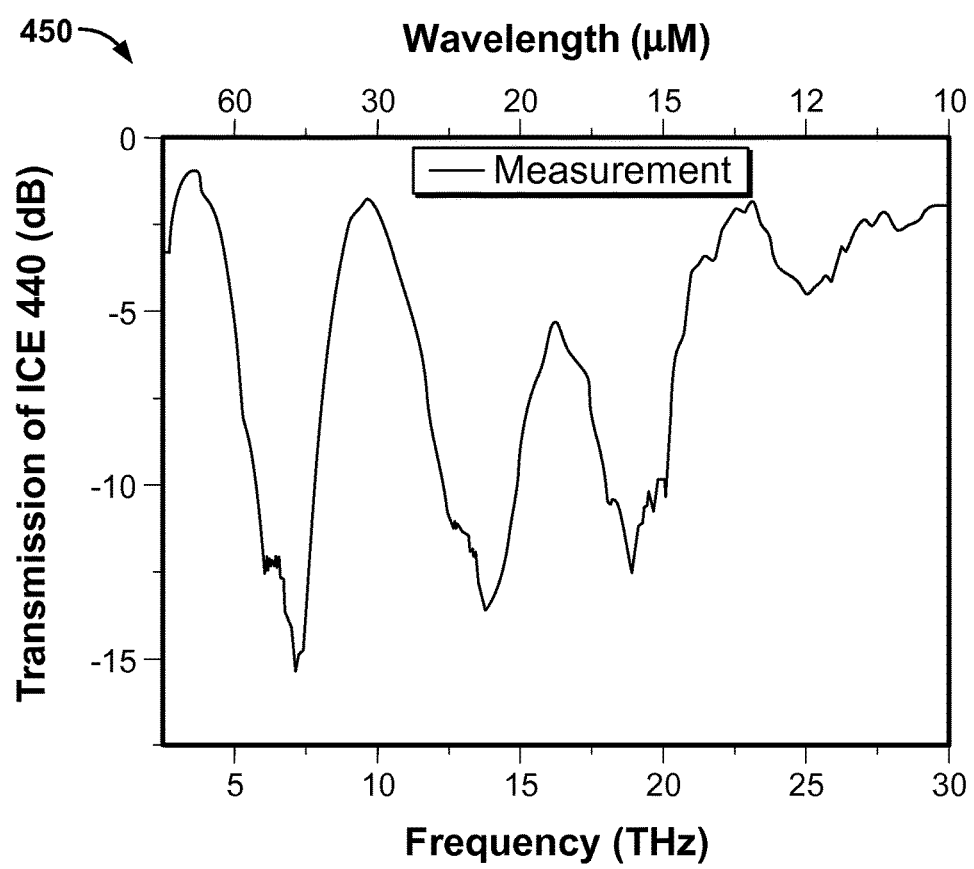

FIGS. 4A-4B show yet another example of an FSS pattern 445 of an ICE 440 and its equivalent filter spectrum filter spectrum $w(\lambda)$ 450. The FSS pattern 445 of the ICE 440 can be designed and fabricated using conventional techniques, as described, for example in the previously cited Bossard reference. FIG. 4A shows that the ICE 440 has an Al layer 444 deposited on a first surface 442 of a polyimide substrate. In this case, a thickness of the polyimide substrate is 4 μm, and a thickness of the Al layer 444 is 75 nm. The FSS pattern 445 has a size of 35.4 μm on a side and includes lateral features of multiple shapes. A quantity of the lateral features of the FSS pattern 445 and their respective shapes are established via a genetic algorithm.

FIG. 4B shows a filter spectrum $w(\lambda)$ 450 equivalent to the FSS pattern 445. In this case, the measured filter spectrum $w(\lambda)$ 450 has a first mid-IR stop band at 14 μm, a second mid-IR stop band at 22 μm, and a far-IR stop band at 50 μm. These three stop bands are respective resonant wavelengths that correspond to particular combinations of lateral dimensions of the lateral features of multiple shapes. This FSS pattern 445 proves that an ICE that has a single metallic layer deposited on the first surface of a dielectric substrate can be configured to have a filter spectrum $w(\lambda)$ with three stop bands in the mid-IR and far-IR.

Figure 5A:
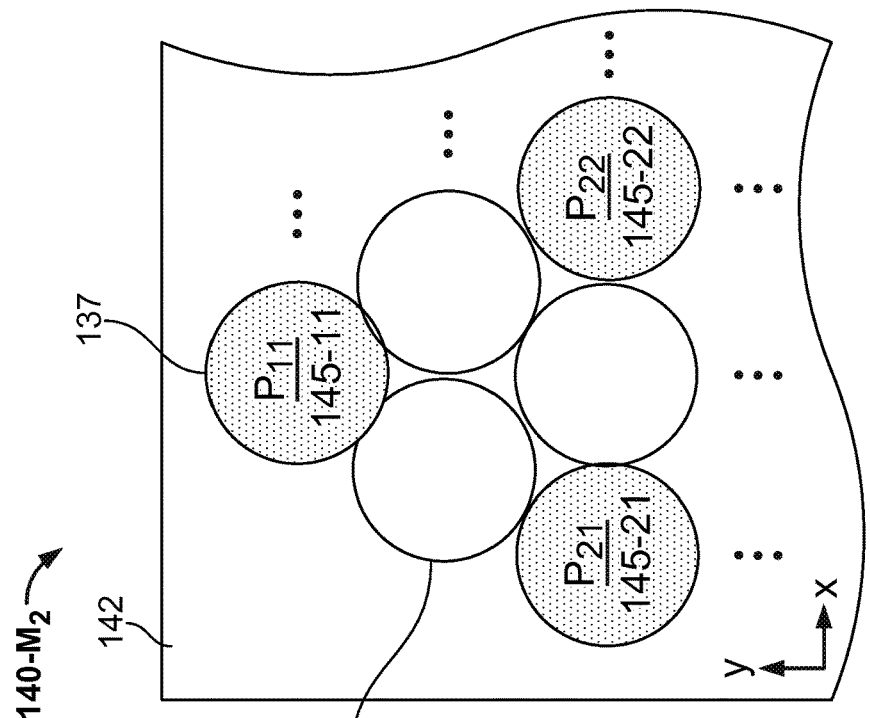
FIG. 5A shows an example of an arrangement of different frequency-selective surface patterns of an ICE.
Figure 5B:
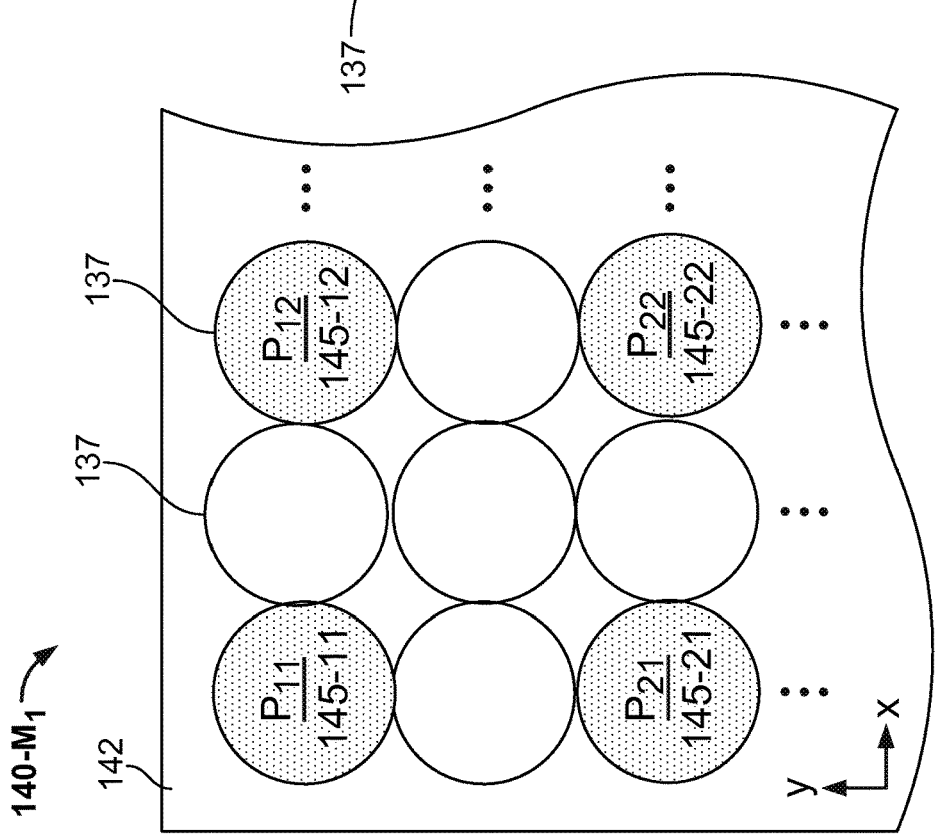
FIG. 5B shows another example of an arrangement of different frequency-selective surface patterns of an ICE.

FIGS. 5A-5B show examples of different arrangements $M_1$, $M_2$ of different FSS patterns 145-$ij$ of two ICEs 140-$M_1$, 140-$M_2$. Portions $P_{ij}$ of the first surface 142 of an ICE 140-$M_1$ (or 140-$M_2$) can be identified based on their location within an arrangement $M_1$ (or $M_2$) of rows. Index "i" is a row label and index "j" is a count within a row. Different rows can have the same or different number of portions $P_{ij}$, and the rows can but need not be offset with respect to each other.

In general, a portion $P_{ij}$ of the first surface 142 of an ICE 140-$M_1$ (or 140-$M_2$) is configured to have a periodic surface pattern 145-$ij$ (also referred to as an FSS pattern 145-$ij$.) A filter spectrum 155-$ij$, which is equivalent with the FSS pattern 145-$ij$, is associated with a property (i,j) of the sample 130. In this manner, the measurement tool 110 that includes the ICE 140-$M_1$ (or 140-$M_2$) can sequentially output values of properties (i,j), as the beam 135 of modified light is laterally scanned over stationary portions $P_{ij}$, or as the portions $P_{ij}$ are laterally translated to cross a stationary beam 135 of modified light.

For example, the portion $P_{11}$ can have the FSS pattern 145 illustrated in FIG. 1 ("145-11"≡145); a filter spectrum 155, which is equivalent with the FSS pattern 145, is associated with a property (1,1) of the sample 130; the property (1,1) can be the concentration of butane in crude petroleum, for instance. As another example, the portion $P_{12}$ can have the FSS pattern 245 illustrated in FIG. 2A ("145-12"≡245); a filter spectrum 255, which is equivalent with the FSS pattern 245, is associated with a property (1,2) of the sample 130; the property (1,2) can be the concentration of methane in crude petroleum, for instance. As yet another example, the portion $P_{21}$ can have the FSS pattern 345 illustrated in FIG. 3A ("145-21"≡345); a filter spectrum 355, which is equivalent with the FSS pattern 345, is associated with a property (2,1) of the sample 130; the property (2,1) can be the pH of crude petroleum, for instance. As another example, the portion $P_{22}$ can have the FSS pattern 445 illustrated in FIG. 4A ("145-22"≡445); a spectral pattern 455, which is equivalent with the frequency-selective surface pattern 445, is associated with a property (2,2) of the sample 130; the property (2,2) can be the viscosity of crude petroleum, for instance. Other FSS patterns, which correspond to other properties of the sample 130, can be configured for the foregoing portions or other portions $P_{ij}$.

As described above, a spot size 137 of the beam 135 of modified light when it reaches the first surface 142 of the ICE is configured, as part of the design process for the measurement tool 110, to include a quantity of structures of the FSS larger than a minimum quantity $N_0$. Moreover, in the case of the ICEs 140$M_1$, 140$M_2$ illustrated in FIGS. 5A-5B, the spot size 137 is configured to be larger than at least $\sqrt{(N_0)} \cdot \max\{d_{11}, d_{12}, d_{21}, d_{22}\}$, where $d_{ij}$ is a lateral dimension associated with the FSS pattern 145-$ij$. In this manner, a spot size 137 larger than 200 μm ($\sqrt{(25)}*40$ μm) can be selected for the ICEs 140$M_1$, 140$M_2$.

A lateral size of a portion $P_{ij}$ is configured to be about equal to a spot size 137 of the beam 135 of modified light when it reaches the first surface 142 of the ICE. In this manner, precious real estate on the first surface 142 of the ICE can be used effectively. Additionally, the portions $P_{ij}$ are distributed over the first surface 142 of the ICE 140-$M_1$ (or 140-$M_2$) such that they are separated from each other by separations that are about equal to the spot size 137. In this manner, the measurement tool 110 can sequentially output values of properties (i,j) as portions $P_{ij}$ of the ICE 140-$M_1$ (or 140-$M_2$) process the beam 135 of modified light independently from adjacent portions $P_{ij}$, $P_{(i\pm1),(j\pm1)}$. Separations between adjacent portions $P_{ij}$, $P_{(i\pm1),(j\pm1)}$ that are smaller than the spot size 137 expose the beam 135 of modified light simultaneously to two different FSS patterns 145-$ij$, 145-($i\pm1$, $j\pm1$). In such case, different equivalent filter spectra 155-$ij$, 155-($i\pm1$, $j\pm1$) of the ICE would simultaneously contribute to the processed spectrum 155'. Such simultaneous contributions to the processed spectrum 155' would be integrated together by the photodetector 160 to generate a value of an arbitrary combination of a property (i,j) with a property ($i\pm1$,$j\pm1$) of the sample 130. Conversely, separations between adjacent portions $P_{ij}$, $P_{(i\pm1),(j\pm1)}$ that are substantially larger than the spot size 137 would unjustifiably increase unused areas of the first surface 142 of the ICE 140-$M_1$ (or 140-$M_2$).

There are a variety of ways to arrange the portions $P_{ij}$ which have sizes comparable to the spot size 137 and are separated from each other by spacings comparable to the spot size 137. FIG. 5A shows a first surface 142 of an ICE 140-$M_1$ onto which portions $P_{ij}$ are distributed based on a square arrangement aligned with the x and y-axes, for instance. In this example, nearest-neighbors of a portion $P_{ij}$ are located along the x and y-axes. Compactness of an arrangement can be quantified as a ratio of (i) a number of portions $P_{ij}$ to (ii) a number of regions that separate the portions $P_{ij}$ from their nearest-neighbor portions $P_{(i\pm1),(j\pm1)}$. In this manner, a compactness of the square arrangement corresponding to the ICE 140-$M_1$ has a value of 4/5=0.8. FIG. 5B shows a first surface 142 of an ICE 140-$M_2$ onto which portions $P_{ij}$ are distributed based on a triangular arrangement, where a base of the triangle is aligned with the x-axis, for instance. In this example, nearest-neighbors of a portion $P_{ij}$ are located along the x-axis and along rays oriented at ±60° and ±120°. A compactness of the triangular arrangement corresponding to the ICE 140-$M_2$ has a value of 3/3=1, which is larger than the value of the compactness of the square arrangement of the ICE 140-$M_1$.

Figure 6A:
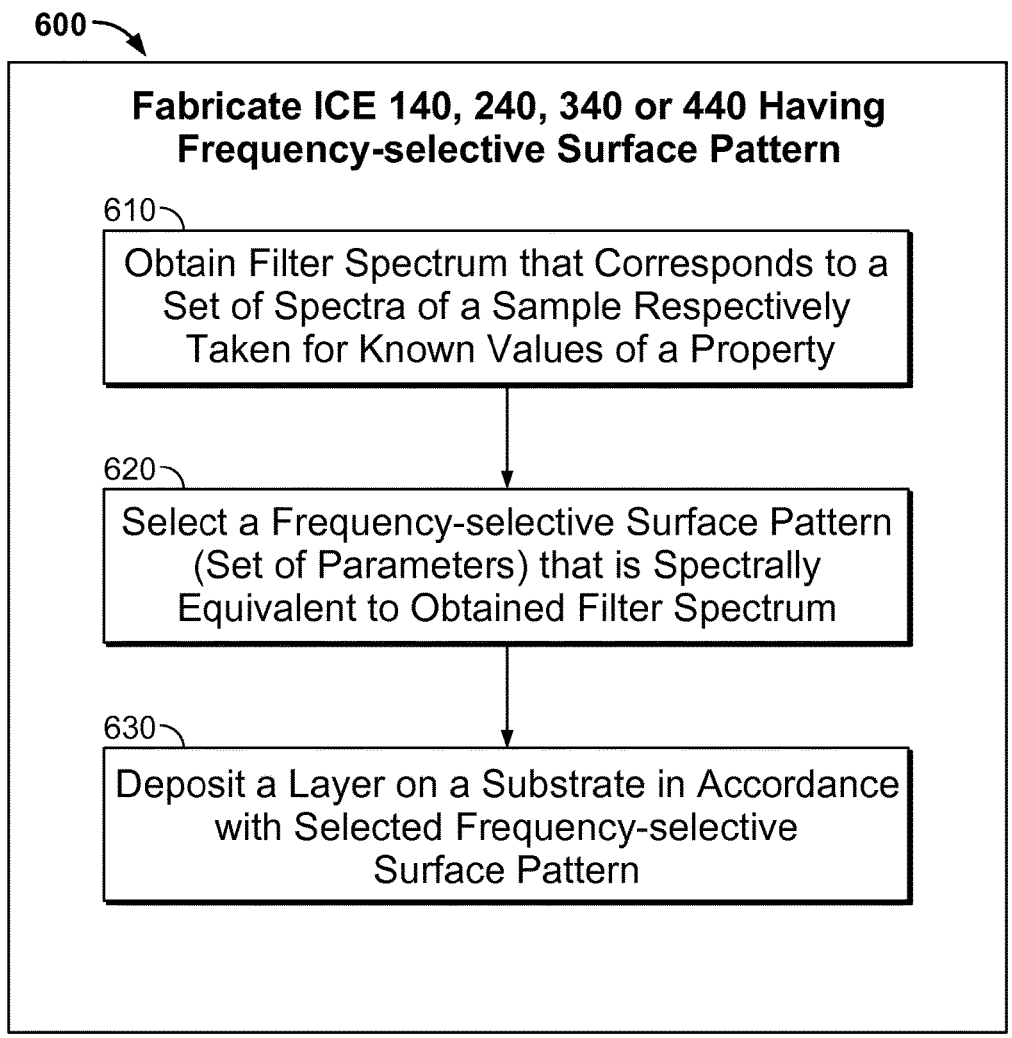
FIG. 6A is a flow chart showing an example of a process for fabricating an ICE that has a frequency selective surface.

In general, ICEs that include a frequency selective surface can be manufactured in a variety of different ways. FIG. 6A is a flow chart showing an example of a process 600 for fabricating an ICE that has a frequency selective surface. In some implementations, the ICE having a frequency selective surface that was fabricated in accordance with the process 600 can be integrated with the measurement tool 110 used in the system 100 for measuring a property of a sample. As such, the ICE that has a frequency selective surface can include a layer of reflective material arranged on a substrate of transparent material.

At 610, a filter spectrum associated with a property of a sample is obtained. In some implementations the sample can be crude petroleum, gas, water, or other wellbore fluids, for instance. The obtained filter spectrum w(λ) 150 corresponds to a set of spectra 135'-j, where j=1–N, of the sample, where the spectra 135'-j were respectively taken for known values of a property of the sample. The property can be any one of multiple physical or chemical properties of the sample including concentration of a given substance in the sample, a gas-oil-ratio (GOR), pH value, density, viscosity, etc.

At 620, an FSS pattern that is spectrally equivalent to the obtained spectral pattern is selected. Such an FSS pattern is used later in the process 600 to deposit a layer of reflective material on a substrate. A material of the substrate can be transparent or opaque to light in a particular wavelength range. In general, the FSS pattern 145 includes lateral features of various shapes, such that the lateral features are arranged in various arrangements. The FSS pattern 145 is selected in terms of a set of parameters that includes: (i) one or more of dimensions of the structures of the frequency-selective surface; (ii) thickness of the reflective layer; (iii) material of the reflective layer (e.g., metal, such as Al); and (iv) material of the substrate (e.g., Si which is transparent in the near-IR, CaF2 which is transparent in the mid-IR, polyimide or diamond which are transparent in the far-IR). Additional parameters that can be used to refine the spectral match between the selected FSS pattern 145 and the obtained filter spectrum w(λ) 150 are (iv) one or more arrangements of the lateral features. Such arrangements can have triangular, rectangular, hexagonal or circular symmetry. A large number of FSS patterns can be generated from the parameters noted above.

Various algorithms can be used to select, from such large number of FSS patterns, one that is spectrally equivalent to the obtained filter spectrum w(λ) 150. In some implementations, an initial guess of values of the parameters is made and an electromagnetic simulation is performed to find a resulting spectrum for the current guessed values of the parameters. The results are compared with the filter spectrum w(λ) 150 and new parameter values are computed in an attempt to find parameters for which an error between the filter spectrum w(λ) 150 and a resultant spectrum is minimized. Any conventional multivariate minimization scheme, such as conjugate gradient, steepest descent, Levenberg-Marquart, and the like, can be used. Several conventional computational methods can be used to generate a spectrum for a given parameter set, such as periodic method of moments, or the finite difference time domain (FDTD) method.

In this manner, an FSS pattern 145 that spectrally produces the desired filter spectrum w(λ) 150 can be designed by varying feature shapes, lateral dimensions, spacing, conductive coating thickness, etc. Electromagnetic modeling may be used iteratively to refine the response of the final design.

In some implementations, a first filter function $w_1(\lambda)$ and a second filter function $w_2(\lambda)$ are obtained, at 610. A birefringent frequency-selective surface can be designed to be equivalent to the obtained first filter function $w_1(\lambda)$ for a first polarization of the modified spectrum 135', and to be equivalent to the obtained second filter function $w_2(\lambda)$ for a second, orthogonal polarization of the modified spectrum 135'. For instance, some of the structures of the birefringent frequency-selective surface that are aligned with the first polarization can be optimized to render the birefringent frequency-selective surface equivalent to the obtained first filter spectrum $w_1(\lambda)$ and some other of the structures that are aligned with the second, orthogonal polarization can be optimized to render the birefringent frequency-selective surface equivalent to the obtained second filter spectrum $w_2(\lambda)$. The optimization techniques described above to determine an FSS pattern equivalent to one filter spectrum can be generalized to determine a birefringent frequency-selective surface that is simultaneously equivalent to each of the first and second filter spectrum $w_1(\lambda)$ and $w_2(\lambda)$.

At 630, a conductive layer is deposited on a first surface of a substrate in accordance with the selected FSS pattern. A conventional metal deposition process can be used to deposit this layer of the ICE. In some implementations, a photomask which encodes a periodic FSS pattern is overlaid on a photoresist-coated substrate. The photomask is configured to include a number of lateral repetitions of the FSS pattern 145 that cover at least a predetermined portion of the photoresist-coated substrate. The photoresist can be (i) developed by exposure to UV light and (ii) partially removed to expose portions of the substrate 141 where the reflective layer 144 will be deposited in accordance with the FSS pattern 145. A metal layer 144 (Al, Cu, Ag, Au, Pt, etc.) can be deposited through thermal evaporation, plasma sputtering, chemical vapor deposition, etc. Then, the photoresist is lifted off to reveal the metal layer 144 patterned in accordance with the FSS pattern 145 on the first surface 142 of the substrate 141.

In this manner, an ICE 140 can be fabricated to include a metal layer 142 deposited on a (transparent or opaque) substrate 141 in accordance with the FSS pattern 145, such that the resulting frequency-selective surface is spectrally equivalent to the obtained filter spectrum w(λ) 150. The ICE 140 fabricated in this manner can be used in the measurement tool 110 to measure a value of a property of a sample, where the property is associated with the filter spectrum w(λ) 150 to which the FSS pattern 145 of the ICE 140 is equivalent.

An ICE with an FSS pattern that is designed and fabricated based on process 600 can go through a design-level calibration process. High reproducibility of conventional photolithographic processes allows for ICEs with the same FSS pattern to be substantially identical. In this manner, only one ICE from among ICEs with the same FSS pattern needs to be calibrated, because the calibration results can be applied to the rest of the ICEs with of the same FSS pattern, regardless of fabrication batch.

Additionally, the process 600 can be used in a piece-meal fashion to fabricate an ICE with a desired filter spectrum $w(\lambda)$ over a given spectral region from $\lambda_1$ to $\lambda_3$. For example, a first metal layer is patterned, in accordance with the fabrication process 600, on a first surface of a support substrate and second metal layer is patterned, in accordance with the fabrication process 600, on a second surface of the support substrate, opposing the first surface. The support substrate can be the substrate 141 shown in FIG. 1. First features of the first patterned layer are configured and arranged in a first laterally periodic array to form a first FSS pattern that is spectrally equivalent to a first filter spectrum $w_1(\lambda)$ over a first spectral region from $\lambda_1$ to $\lambda_2$, where $\lambda_2 < \lambda_3$, e.g., in the near-IR. Second features of the second patterned layer are configured and arranged in a second laterally periodic array to form a second FSS pattern that is spectrally equivalent to a second filter spectrum $w_2(\lambda)$ over a second spectral region from $\lambda_2$ to $\lambda_3$, e.g., in the mid-IR. In this manner, the desired filter spectrum $w(\lambda)$ associated with the ICE is composed from the first filter spectrum $w_1(\lambda)$ to which the first FSS pattern is equivalent over the first spectral region from $\lambda_1$ to $\lambda_2$, and the second filter spectrum $w_2(\lambda)$ to which the second FSS pattern is equivalent over the second spectral region from $\lambda_2$ to $\lambda_3$.

Figure 6B:
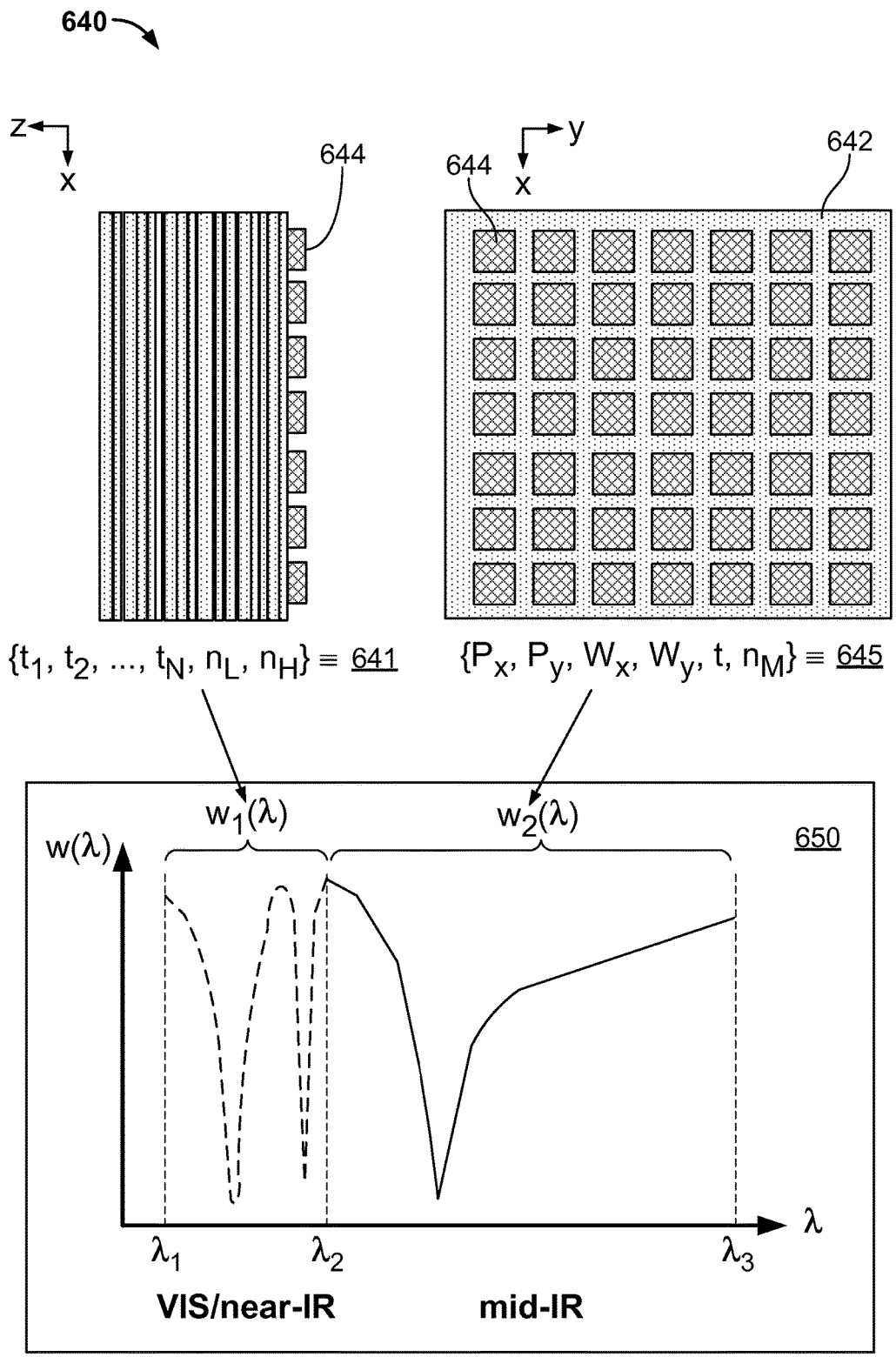
FIG. 6B shows aspects of an example of a conventional ICE that has a frequency-selective surface and an extended filter spectrum of the ICE.

FIG. 6B shows how the fabrication process 600 can be used to extend a filter spectrum $w_1(\lambda)$ of a conventional ICE, and thus enhance its functionality. A conventional ICE can be fabricated as a dielectric interference filter from a substrate 641 that includes N>30 layers of two materials (e.g., $SiO_2$ and $Nb_2O_5$) with different indices of refraction, a low index of refraction $n_L$, and a high index of refraction $n_H$, such that the N layers of the conventional ICE are interlaced along the z-axis. The number N of layers, thickness thereof $\{t_1, t_2, \ldots, t_N\}$, and the indexes of refraction $n_L$ and $n_H$ of the two materials of the substrate 641 define the filter spectrum $w_1(\lambda)$ of the conventional ICE over a spectral range from $\lambda_1$ to $\lambda_2$, e.g., through UV-vis and near-IR.

In the example illustrated in FIG. 6B, a modified ICE 640 can be fabricated, in accordance with the process 600, by depositing a metal layer 644 on a first surface 642 of the conventional ICE to form an FSS of the modified ICE 640. In some implementations, the metal layer 644 is deposited as a periodic array (in the x-y plane) of patches 645 (also referred to as an FSS pattern 645.) A thickness "t" of the metal layer 644 along with widths $w_x$, $w_y$ and periods $p_x$, $p_y$ of the patches render the FSS pattern 645 spectrally equivalent to an extended filter spectrum $w_2(\lambda)$. The extended filter spectrum $w_2(\lambda)$ can have spectral features over an extended spectral region from $\lambda_2$ to $\lambda_3$, e.g., through mid-IR. In this manner, a modified filter spectrum $w(\lambda)$ 650 of the modified ICE 640 is composed of the filter spectrum $w_1(\lambda)$ of the conventional ICE (represented by dotted curve) and the extended filter spectrum $w_2(\lambda)$ (represented by solid curve) to which the FSS pattern 645 is equivalent.

In other implementations, not illustrated in FIG. 6B, the functionality of the ICE 640 can be further enhanced by further extending its filter spectrum $w(\lambda)$, for example over a spectral region from $\lambda_3$ to $\lambda_4$, e.g., through far-IR. The further extension can be accomplished, in accordance with the process 600, by depositing a second metal layer on a second surface of the conventional ICE (opposing the first surface 642) to form a second FSS of the modified ICE 640. Parameters of the second FSS define a second FSS pattern that is spectrally equivalent to a second extended filter spectrum $w_3(\lambda)$ over the spectral region from $\lambda_3$ to $\lambda_4$. Such a modified filter spectrum $w(\lambda)$ of the modified ICE is composed of the filter spectrum $w_1(\lambda)$ of the conventional ICE (over the spectral region from $\lambda_1$ to $\lambda_2$) the extended filter spectrum $w_2(\lambda)$ (over the spectral region from $\lambda_2$ to $\lambda_3$) to which the FSS pattern 645 is equivalent, and the second extended filter spectrum $w_3(\lambda)$ (over the spectral region from $\lambda_3$ to $\lambda_4$) to which the second FSS pattern is equivalent.

Figure 6C:
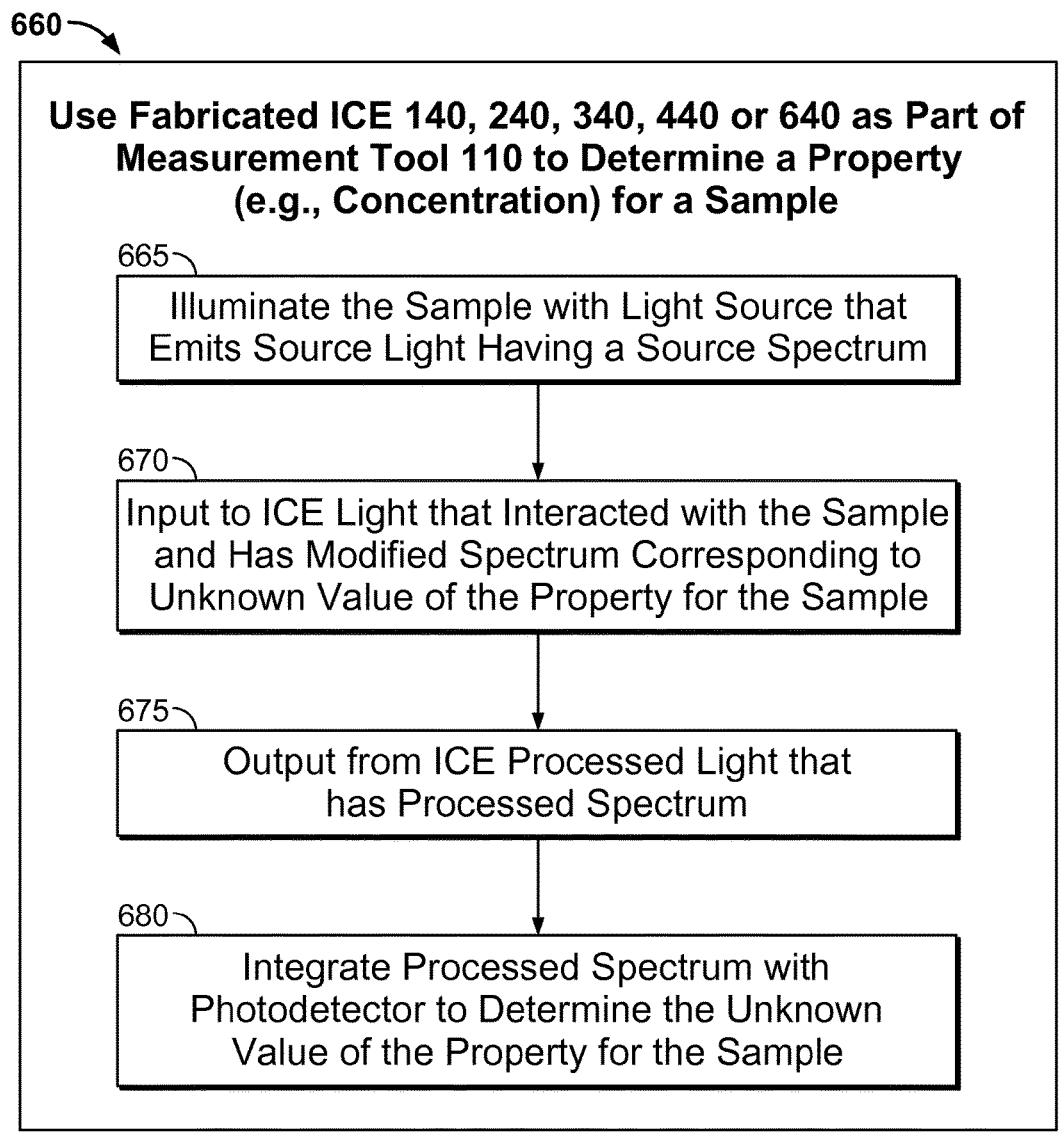
FIG. 6C is a flow chart showing an example of a process for measuring a property of a sample using an ICE that has a frequency selective surface.

FIG. 6C is a flow chart showing an example of a process 660 for measuring a property of a sample using an ICE that has a frequency selective surface. In some implementations, the process 660 can be performed by the measurement tool 110 as part of the system 100 and will be described as such for the purpose of clarity. For example, the sample 130 can be crude petroleum or other wellbore fluid that is stationary in or flows through the pipe 38.

At 665, the sample 130 is illuminated with a light source 120 that emits source light having a source spectrum $I_0(\lambda)$ 125. The source spectrum $I_0(\lambda)$ 125' can be continuous over a broad wavelength range. For example, the wavelength range can span UV-vis, near-IR, mid-IR and far-IR.

At 670, light that interacted with and was modified by the sample 130 is input to an ICE 140 that has an FSS pattern 145. The light modified by the sample has spectrum $I(\lambda)$ 135' corresponding to an unknown value of the property of the sample 130. The FSS pattern 145 is spectrally equivalent to a filter spectrum $w(\lambda)$ 150 over the wavelength range. The filter spectrum $w(\lambda)$ 150 corresponds to a set of spectra of the sample respectively taken for known values of the property.

At 675, processed light is output from the ICE 140. The ICE 140 generates a processed spectrum $P(\lambda)$ 155' by weighing the modified spectrum $I(\lambda)$ 135' with the filter spectrum $w(\lambda)$ 150 to which the ICE 140's FSS pattern 145 is equivalent. In this manner, the processed light has a processed spectrum $P(\lambda)=w(\lambda)I(\lambda)$ 155' over the wavelength range.

At 680, the processed spectrum $P(\lambda)$ 155' is integrated with a photodetector 160 over the wavelength range to determine the unknown value c 165' of the property for the sample.

In general, the ICEs described herein can be used in a variety of applications. As mentioned previously, in some applications, ICEs are used to measure properties of fossil fuel samples in situ, e.g., down hole during oil and gas drilling and/or extraction.

Figure 7:
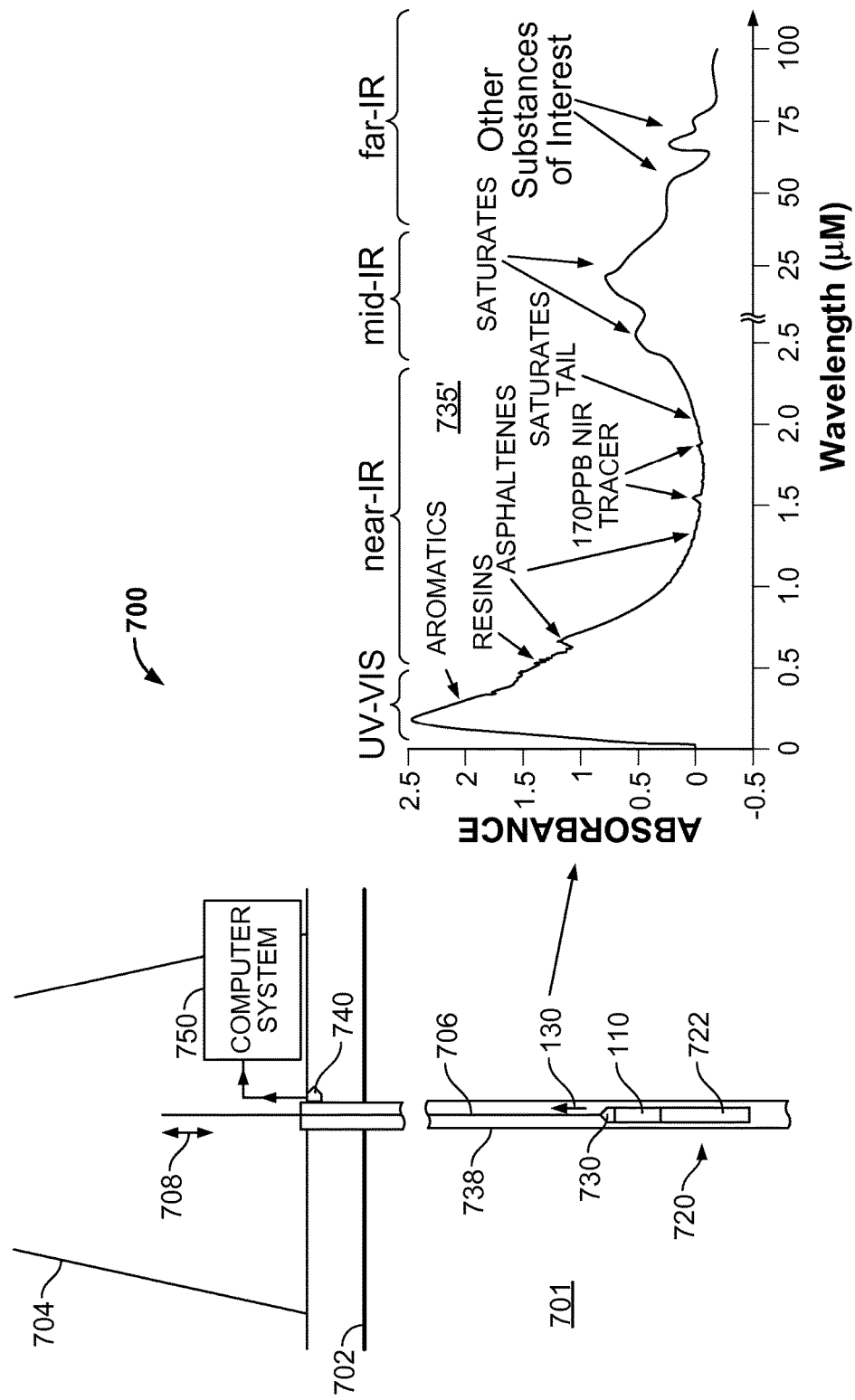
FIG. 7 shows an example of a system for in-situ measuring of crude petroleum, gas, water, or other wellbore fluids, where the measurement is performed using the system of FIG. 1.

FIG. 7 shows an example of a system 700 for down hole measurements, where at least some of the measurements are performed using the measurement tool 110 of FIG. 1.

The system 700 includes a rig 704 above the ground surface 702 and a wellbore 738 below the ground surface. The wellbore 738 extends from the ground surface into the earth and generally passes through multiple geologic formations 701. In general, the wellbore 738 contains wellbore fluids 130. In some cases, the wellbore fluids 130 include crude petroleum. However, the wellbore fluids 130 may include mud, water or other substances and/or compounds. Moreover, the crude petroleum, gas, water, or other wellbore fluid 130 may be at rest, or may flow toward the ground surface 702, for instance. A tool string 720 is attached to a cable 706 and can be lowered or raised in the wellbore 738 by draw works 708. In general, the tool string 720 includes measurement and logging tools configured to generate and log information about the geologic formations outside of the wellbore 738 and/or about the crude petroleum, gas, water, or other wellbore fluids 130 in the wellbore 738. In this example, the tool string 720 includes the measurement tool 110 described above in connection with FIG. 1, one or more logging tool(s) 722, and a telemetry transmitter 730. The measurement tool 110 includes an ICE that has a frequency selective surface and is configured to measure one or more properties of crude petroleum, gas, water, or other wellbore fluids 130.

In some implementations, the measurement tool 110 determines values of the one or more properties in real time and reports those values instantaneously as they occur in the flowing stream of wellbore fluids 130, sequentially to or simultaneously with other measurement/logging tools 722 of the tool string 720. Measured values (e.g., 165' in FIG. 1) of the one or more properties of the wellbore fluids 130 can be provided (e.g., as detector signal 165) to the telemetry transmitter 730. The latter communicates the measured values to a telemetry receiver 740 located above the ground surface 702. The transmitter 730 and the receiver 740 can communicate through wires or wirelessly. The measured values of the one or more properties of the wellbore fluids 130 received by the receiver 740 can be logged and analyzed by a computer system 750 associated with the rig 704. In this manner, the values provided by the measurement tool 110 can be used to generate useful physical and chemical information about the wellbore fluids 130 in the wellbore 38.

As described above, a light source included in the measurement tool 110 illuminates the wellbore fluids 130 with light source that can extend over the UV-vis, near-IR, mid-IR and far-IR spectral ranges (e.g., in the wavelength range from 0.2-100 μm.) The source light is modified by the interaction with the wellbore fluids 130 to produce a modified spectrum 735'. In this manner, the modified spectrum 735' contains information about one or more properties of the wellbore fluids. In order to extract such information from the modified spectrum 735', light that interacted with the wellbore fluids is directed to an ICE (e.g., 140, 240, 340, 440, 140-M1, 140-M2) that has an FSS pattern (e.g., 145, 245, 345, 445, and combinations thereof) for processing. The ICE weighs the modified spectrum 735', with a filter spectrum (e.g., 150, 250, 350, 450, and combinations thereof) to which the FSS pattern is equivalent, and generates a processed spectrum corresponding to a property associated with the filter spectrum. A value of the property is determined by a photodetector that integrates the processed spectrum.

Properties of the wellbore fluids 130 that can be related to the modified spectrum 735' through the filter spectra associated with the ICEs described herein are concentrations of one of asphaltene, saturates, resins, aromatics; solid particulate content; hydrocarbon composition and content; gas composition C1-C6 and content: CO2, $H_2S$ and correlated PVT properties including GOR, bubble point, density; a petroleum formation factor; viscosity; a gas component of a gas phase of the petroleum; total stream percentage of water, gas, oil, solid articles, solid types; oil finger printing; reservoir continuity; oil type; and water elements including ion composition and content, anions, cations, salinity, organics, pH, mixing ratios, tracer components, contamination, or other hydrocarbon, gas, solids or water property.

The measurement tool 110 may be deployed as part of a measurement while drilling tool, a wireline based formation evaluation tool, (i) in an autonomous mode where data and meta-data is written to memory or sent via various telemetry methods, (ii) in a permanent installation mode where the sensor is part of the production tubular telemetry or is part of a smart well completion and data network, electric or fiber and may or may not be retrievable. Surface applications of the measurement tool 110 may include water monitoring and gas and crude transportation and processing.

Some embodiments have been described in detail above, and various modifications are possible. While this specification contains many specifics, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Other embodiments fall within the scope of the following claims.

What is claimed is:

1. A system comprising:
a light source that illuminates, during operation of the system, a sample with light having a source spectrum over a wavelength range to obtain light modified by the sample, wherein the light modified by the sample has a modified spectrum over the wavelength range, the modified spectrum corresponding to the sample;
an integrated computational element (ICE) comprising
a substrate having a surface, and
a layer disposed on the surface of the substrate as a frequency-selective surface pattern, wherein the frequency-selective surface pattern is defined in terms of a set of parameters to be spectrally equivalent to a filter spectrum over the wavelength range, wherein the filter spectrum corresponds to a set of spectra of the sample respectively taken for known values of a property of the sample, wherein the ICE (i) is arranged to receive the light modified by the sample and (ii) outputs processed light having a processed spectrum over the wavelength range; and
a photodetector optically coupled with the ICE to receive the processed light, wherein the photodetector integrates the processed spectrum over the wavelength range to determine a current value of the property of the sample.

2. The system of claim 1, wherein the set of parameters comprises one or more of dimensions of lateral features of the frequency-selective surface pattern, thickness of the layer, material of the layer and material of the substrate on which the layer is disposed.

3. The system of claim 2, wherein the set of parameters further comprises one or more arrangements of the lateral features of the frequency-selective surface pattern, the arrangements having triangular, rectangular, hexagonal or circular symmetry.

4. The system of claim 2, wherein values of the dimensions of the lateral features respectively correspond to spectral features of the filter spectrum.

5. The system of claim 4, wherein values of the set of parameters determine the wavelength range of the spectral features of the filter spectrum to be from 0.2 to 100 µm.

6. The system of claim 2, wherein
first dimensions from among the dimensions of the lateral features respectively correspond to first spectral features of the filter spectrum associated with a first polarization component of the light modified by the sample, and second dimensions from among the dimensions of the lateral features that are orthogonal on and have different values from values of the first dimensions respectively correspond to second spectral features of a second filter spectrum associated with a second, orthogonal polarization component of the light modified by the sample, and
the second filter spectrum corresponds to a second set of spectra of the sample respectively taken for known values of a second property.

7. The system of claim 1, wherein the frequency-selective surface pattern is laterally periodic over a predetermined portion of the surface of the substrate.

8. The system of claim 7, wherein the frequency-selective surface pattern comprises a periodic array of conductive patches, such that inside the conductive patches there are one or more apertures.

9. The system of claim 7, wherein the frequency-selective surface pattern comprises a conductive layer with an array of apertures therein, such that inside the apertures there are one or more conducting patches.

10. The system of claim 7, wherein
the layer is disposed on the surface of the substrate as the frequency-selective surface pattern and one or more additional frequency-selective surface patterns, and
each of the additional frequency-selective surface patterns
is defined in terms of an associated set of parameters to be spectrally equivalent to an associated filter spectrum over the wavelength range, such that the associated filter spectrum corresponds to an associated set of spectra of the sample respectively taken for known values of an additional associated property, and
is laterally periodic over an associated other predetermined portion of the surface of the substrate, such that other predetermined portions of the surface of the substrate corresponding to the respective additional frequency-selective surface patterns are laterally separated, from each other and from the predetermined portion corresponding to the frequency-selective surface pattern, by separations at least a size of a spot size when the light modified by the sample is received at the ICE.

11. The system of claim 7, wherein, when the light modified by the sample is received at the ICE, a spot size encompasses at least a threshold quantity of repetitions of the frequency-selective surface pattern.

12. The system of claim 11, wherein the threshold quantity of repetitions of the frequency-selective surface pattern is about 25 repetitions.

13. A measurement tool comprising:
an optical element comprising a layer of material that is patterned to be spectrally equivalent to a filter spectrum over a wavelength range, the optical element configured to process, during an operation of the measurement tool, light in at least a portion of the wavelength range using the layer of patterned material, the filter spectrum being based on a set of spectra that correspond to respective known values of a property of a sample to be measured.

14. The measurement tool of claim 13, wherein the wavelength range comprises wavelengths in a range from about 0.2 µm to about 25 µm.

15. The measurement tool of claim 13, wherein the sample comprises wellbore fluids and the property of the sample is a property of the wellbore fluids.

16. The measurement tool of claim 15, wherein the property of the sample is selected from the group consisting of a concentration of a substance in the sample, a pH of the sample, a ratio of concentrations of two different substances in the sample, a density of the sample, and a viscosity of the sample.

17. The measurement tool of claim 13, wherein the optical element comprises a substrate supporting the layer of patterned material and the layer of patterned material comprises a plurality of identical features arranged in an array on a first surface of the substrate.

18. The measurement tool of claim 17, wherein the features each comprise one or more geometric shapes selected from the group consisting of triangles, quadrilaterals, hexagons, and circles.

19. The measurement tool of claim 17, wherein
the optical element further comprises another layer of patterned material supported on a second surface of the substrate opposing the first surface,
the other layer of patterned material comprises a plurality of identical other features arranged in another array on the second surface,
the optical element selectively transmits or reflects differing amounts of light in (i) a first portion of the wavelength range in accordance with the array of the identical features of the layer of patterned material supported on the first surface, and (ii) a second portion of the wavelength range in accordance with the other array of the identical other features of the other layer of patterned material supported on the second surface.

20. The measurement tool of claim 17, wherein
the substrate of the optical element comprises a dielectric interference filter, and
the optical element selectively transmits or reflects differing amounts of light in (i) a first portion of the wavelength range in accordance with the array of the identical features of the layer of patterned material, and (ii) a second portion of the wavelength range in accordance with the dielectric interference filter.

21. The measurement tool of claim 20, wherein
the optical element further comprises another layer of patterned material supported on a second surface of the substrate opposing the first surface,
the other layer of patterned material comprises a plurality of identical other features arranged in another array on the second surface,
the optical element selectively transmits or reflects differing amounts of light in (i) the first portion of the wavelength range, (ii) the second portion of the wavelength range, and (iii) a third portion of the wavelength range in accordance with the other array of the identical other features of the other layer of patterned material supported on the second surface.

22. The measurement tool of claim 13, further comprising:
   a light source positioned to illuminate the sample with light having a first spectrum over the wavelength range, wherein the optical element is positioned to receive light from the sample in response to the illumination, such that the light received from the sample has a second spectrum over the wavelength range, the second spectrum corresponding to the first spectrum modified by the sample; and
   a detector positioned to receive light from the optical element and produce a signal having a value related to an integrated intensity of the light from the optical element across the wavelength range, wherein the signal value corresponds to a value of the property of the sample.

23. The measurement tool of claim 22, further comprising a transparent element positioned in a path of the light between the light source and the sample.

24. The measurement tool of claim 23, wherein the optical element is positioned to receive light reflected from an interface between the sample and the transparent element.

25. A method, comprising:
placing a measurement tool in a wellbore, said measurement tool comprising:
   a light source positioned to illuminate a sample with light having a first spectrum over a wavelength range;
   an optical element positioned to receive light from the sample in response to the illumination and configured to produce processed light from the light received from the sample, wherein the light received from the sample has a second spectrum over the wavelength range, the second spectrum corresponding to the first spectrum modified by the sample; and
   a detector positioned to receive the processed light from the optical element and produce a signal having a value related to an integrated intensity of the light from the optical element across the wavelength range, wherein the signal value corresponds to a value of a property of the sample; and
determining the value of the property of the sample in the wellbore using the measurement tool.

* * * * *